(12) United States Patent
Fukunaga

(10) Patent No.: US 10,342,417 B2
(45) Date of Patent: Jul. 9, 2019

(54) IMAGE-CAPTURING ELEMENT

(71) Applicant: OLYMPUS CORPORATION, Hachioji-shi, Tokyo (JP)

(72) Inventor: Yasuhiro Fukunaga, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 371 days.

(21) Appl. No.: 15/156,917

(22) Filed: May 17, 2016

(65) Prior Publication Data
US 2016/0256039 A1 Sep. 8, 2016

Related U.S. Application Data

(63) Continuation of application No. PCT/JP2014/076073, filed on Sep. 30, 2014.

(30) Foreign Application Priority Data

Nov. 20, 2013 (JP) .................................. 2013-239903

(51) Int. Cl.
A61B 1/00 (2006.01)
H01L 27/146 (2006.01)
(Continued)

(52) U.S. Cl.
CPC .......... *A61B 1/00186* (2013.01); *A61B 1/043* (2013.01); *A61B 1/051* (2013.01);
(Continued)

(58) Field of Classification Search
CPC ..... A61B 1/00186; A61B 1/043; A61B 1/051; H01L 27/14621; H01L 27/14625;
(Continued)

(56) References Cited

U.S. PATENT DOCUMENTS 4,820,028 A * 4/1989 Suda ...................... G02B 15/16
359/676
5,159,199 A 10/1992 LaBaw
(Continued)

FOREIGN PATENT DOCUMENTS

JP 6-204445 A 7/1994
JP 11-297973 A 10/1999
(Continued)

OTHER PUBLICATIONS

International Search Report dated Dec. 16, 2014, issued in counterpart International Application No. PCT/JP2014/076073, w/English translation (4 pages).
(Continued)

*Primary Examiner* — Nathnael Aynalem
(74) *Attorney, Agent, or Firm* — Westerman, Hattori, Daniels & Adrian, LLP

(57) ABSTRACT

An image-capturing element includes: a first substrate; a plurality of first pixels disposed in a matrix on the first substrate, each of the first pixels having a first light receiving element; a second substrate disposed at a position overlapping the first substrate and on a side opposite to a light receiving surface side of the first substrate when viewed from the light receiving surface side of the first substrate; a plurality of second pixels disposed in a matrix on the second substrate, each of the second pixels having a second light receiving element and a Fabry-Perot filter disposed on the light receiving surface side of the second light receiving element; and a plurality of optical systems disposed corresponding to the plurality of second pixels between the first substrate and the plurality of second pixels, the optical systems having negative refractive power.

14 Claims, 25 Drawing Sheets

(51) Int. Cl.
*H04N 5/369* (2011.01)
*H04N 9/04* (2006.01)
*A61B 1/04* (2006.01)
*A61B 1/05* (2006.01)
*H04N 9/07* (2006.01)
*H04N 5/225* (2006.01)

(52) U.S. Cl.
CPC .. *H01L 27/14621* (2013.01); *H01L 27/14625* (2013.01); *H01L 27/14627* (2013.01); *H01L 27/14634* (2013.01); *H04N 5/369* (2013.01); *H04N 9/045* (2013.01); *H04N 9/07* (2013.01); *H04N 2005/2255* (2013.01)

(58) Field of Classification Search
CPC ......... H01L 27/14627; H01L 27/14634; H01L 27/14632; H01L 27/14636; H01L 27/1464; H01L 27/14645; H01L 31/02162; H04N 2005/2255; H04N 9/045; H04N 9/07; H04N 5/2253; H04N 5/2254; H04N 5/33; F21Y 2115/10; G01J 2003/2806; G01J 2003/2826; G01J 3/02; G01J 3/0256; G01J 3/26; G01J 3/2803; G01J 3/2823
See application file for complete search history.

(56) References Cited

U.S. PATENT DOCUMENTS

| | | | |
|---|---|---|---|
| 5,453,611 A | 9/1995 | Oozu et al. | |
| 8,077,255 B2* | 12/2011 | Shintani | G02B 7/34 348/360 |
| 2004/0141182 A1* | 7/2004 | Schroder | G01J 3/26 356/454 |
| 2005/0068541 A1* | 3/2005 | Gunning | G01J 3/26 356/519 |
| 2009/0008532 A1 | 1/2009 | Setoguchi | |
| 2011/0007306 A1* | 1/2011 | Jak | G01J 1/02 356/225 |
| 2011/0102653 A1 | 5/2011 | Shintani et al. | |
| 2011/0109232 A1* | 5/2011 | Schulz | G01J 1/02 315/151 |
| 2013/0057699 A1 | 3/2013 | Ooki | |
| 2013/0075607 A1 | 3/2013 | Bikumandla et al. | |
| 2014/0191357 A1 | 7/2014 | Lee | |

FOREIGN PATENT DOCUMENTS

| | | |
|---|---|---|
| JP | 2007-67075 A | 3/2007 |
| JP | 2008-227250 A | 9/2008 |
| JP | 2013-70030 A | 4/2013 |
| JP | 2013-085028 A | 5/2013 |
| WO | 2007/086352 A1 | 8/2007 |
| WO | 2010/050184 A1 | 5/2010 |
| WO | 2013/022269 A2 | 2/2013 |

OTHER PUBLICATIONS

Notice of Allowance dated May 30, 2017, issued in counterpart Japanese Patent Application No. 2013-239903, with English translation. (6 pages).

* cited by examiner

IMAGE-CAPTURING ELEMENT

This application is a continuation application based on a PCT International Application No. PCT/JP2014/076073, filed on Sep. 30, 2014, whose priority is claimed on Japanese Patent Application No. 2013-239903, filed Nov. 20, 2013. Both of the content of the PCT International Application and the Japanese Application are incorporated herein by reference.

BACKGROUND OF THE INVENTION

Field of the Invention

The present invention relates to an image-capturing element.

Description of Related Art

In regard to a method of diagnosing cancer, active research using a fluorochrome represented by indocyanine green (ICG) has been published in recent years. A technique in which a filter using Fabry-Perot interference is integrally formed on an image sensor as an optical element which detects light having a specific wavelength, such as fluorescence, is known (for example, see U.S. Pat. No. 5,159,199).

An image-capturing element with a hybrid structure in which two layers of an image-capturing element are laminated and imaging is also performed in a lower layer using light transmitted through an upper layer is known (for example, see United States Patent Application, Publication No. 2013/0075607).

Hereinafter, the technique described in U.S. Pat. No. 5,159,199 will be described referring to FIGS. 20 and 21. FIG. 20 is a schematic view showing an example of pixels (Fabry-Perot filter pixels), in each of which a Fabry-Perot filter is formed on a pixel of a conventional image sensor.

In the example shown in FIG. 20, a plurality of pixels F1 to F8 are formed on a semiconductor substrate. A photodiode (PD) 5*d* is formed in each of the pixels F1 to F8. On the light receiving surface of each of the pixels F1 to F8, dielectric layers 5*a* and 5*c* and an interlayer film 5*b* as a Fabry-Perot filter are formed. The interlayer films 5*b* formed in the respective pixels F1 to F8 are sandwiched between the dielectric layers 5*a* and 5*c*, and are different in thickness in order to change the wavelength band of light with which the photodiode 5*d* formed in each of the pixels F1 to F8 is irradiated. With this configuration, for example, as shown in FIG. 21, each of the pixels F1 to F8 can detect light of a narrow transmission band.

FIG. 21 is a graph showing the wavelength of light transmitted through a conventional Fabry-Perot filter. The horizontal axis of the graph shown in FIG. 21 indicates wavelength, and the vertical axis of the graph indicates transmittance. In the example shown in FIG. 21, the Fabry-Perot filter (the dielectric layers 5*a* and 5*c* and the interlayer film 5*b*) formed in the pixel F1 transmits light having a wavelength of a narrow band near 420 nm. For this reason, the pixel F1 can detect light having a wavelength of a narrow band near 420 nm. Similarly to the pixel F1, the pixels F2 to F8 can detect light having a wavelength of a narrow band according to light having a wavelength transmitted through the dielectric layers 5*a* and 5*c* and the interlayer film 5*b* formed therein. The bands of light transmitted through the dielectric layers 5*a* and 5*c* and the interlayer film 5*b* formed in the respective pixels F2 to F8 are as shown in FIG. 21.

Hereinafter, the technique described in United States Patent Application, Publication No. 2013/0075607 will be described referring to FIG. 22. FIG. 22 is a sectional view showing a conventional image-capturing element with a hybrid structure in which two layers of an image-capturing element are laminated and imaging is also performed in a lower layer using light transmitted through an upper layer. In the example shown in FIG. 22, a first substrate 221 and a second substrate 222 are laminated. First photodiodes 223-1 to 223-*m* are formed on the upper first substrate 221. Second photodiodes 224-1 to 224-*m* are formed on the lower second substrate 222.

With this configuration, light transmitted through the first photodiodes 223-1 to 223-*m* formed on the upper first substrate 221 can be received by the second photodiodes 224-1 to 224-*m* formed on the lower second substrate 222. Accordingly, imaging can be performed simultaneously by the first photodiodes 223-1 to 223-*m* formed on the first substrate 221 and the second photodiodes 224-1 to 224-*m* formed on the second substrate 222.

Hereinafter, an example where the technique described in U.S. Pat. No. 5,159,199 and the technique described in United States Patent Application, Publication No. 2013/0075607 are combined will be described. FIG. 23 is a sectional view showing an image-capturing element in which a Fabry-Perot filter is constituted on a lower substrate of a two-layered image-capturing element. In the example shown in FIG. 23, an image-capturing element 230 includes a first substrate 231, a second substrate 232, first photodiodes 233-1 to 233-*m*, second photodiodes 234-1 to 234-*m*, color filters 235-1 to 235-*m*, Fabry-Perot filters 236-1 to 236-*m*, and microlenses 237-1 to 237-*m*.

The first photodiodes 233-1 to 233-*m* are disposed inside the first substrate 231. The color filters 235-1 to 235-*m* are disposed on the light receiving surface side of the first photodiodes 233-1 to 233-*m*. Sets of the first photodiodes 233-1 to 233-*m* and the color filters 235-1 to 235-*m* are respectively referred to as first pixels 239-1 to 239-*m*. For example, a set of the first photodiodes 233-1 and the color filter 235-1 is referred to as the first pixel 239-1.

The second photodiodes 234-1 to 234-*m* are disposed inside the second substrate 232. The Fabry-Perot filters 236-1 to 236-*m* are disposed on the light receiving surface side of the second photodiodes 234-1 to 234-*m*. Sets of the second photodiodes 234-1 to 234-*m* and the Fabry-Perot filters 236-1 to 236-*m* are respectively referred to as second pixels 240-1 to 240-*m*. For example, the set of the second photodiode 234-1 and the Fabry-Perot filter 236-1 is referred to as the second pixel 240-1.

The microlenses 237-1 to 237-*m* are disposed on the light receiving surface side of the first substrate 231 corresponding to the first pixels 239-1 to 239-*m*. For example, the microlens 237-1 is disposed on the light receiving surface side of the first substrate 231 corresponding to the first pixel 239-1. The first substrate 231 and the second substrate 232 are silicon substrates. The first substrate 231 transmits part of light incident thereon. The first photodiodes 233-1 to 233-*m* output first signals according to the exposure. The second photodiodes 234-1 to 234-*m* output second signals according to the exposure.

Each of the color filters 235-1 to 235-*m* is one of a color filter R which transmits light of red (R), a color filter G which transmits light of green (G), and a color filter B which transmits light of blue (B). The arrangement of the color filters 235-1 to 235-*m* will be described below.

The Fabry-Perot filters 236-1 to 236-m transmit light of a predetermined narrow band. For example, the Fabry-Perot filters 236-1 to 236-m transmit light of a narrow band centering on 830 nm. The Fabry-Perot filters 236-1 to 236-m which transmit light of a narrow band centering on 830 nm are referred to as Fabry-Perot filters F. The microlenses 237-1 to 237-m condense incident light and irradiate the corresponding first pixels 239-1 to 239-m with condensed light.

Next, the arrangement of the color filters 235 and the arrangement of the Fabry-Perot filters 236 will be described. FIG. 24 is a schematic view showing the arrangement of the color filters 235 and the arrangement of the Fabry-Perot filters 236. In the example shown in FIG. 24, the first substrate 231 includes 36 first pixels 239 in total regularly arranged in a two-dimensional manner of six rows and six columns. The second substrate 232 includes the 36 second pixels 240 regularly arranged in a two-dimensional manner of six rows and six columns.

As shown in FIG. 24, the color filters 235 (color filters R, color filters G, and color filters B) are arranged in a Bayer array on the first substrate 231. The same Fabry-Perot filters 236 (Fabry-Perot filters F) are arranged on the second substrate 232.

Next, the spectral characteristics of the color filters 235 and the Fabry-Perot filter 236 will be described. FIG. 25 is a graph showing the spectral characteristics of the conventional color filters 235 and the conventional Fabry-Perot filter 236. The horizontal axis of the graph indicates wavelength (nm). The vertical axis of the graph indicates transmittance. A curve 2501 indicates the transmittance of the color filter R, which transmits light of red (R), among the color filters 235. A curve 2502 indicates the transmittance of the color filter G, which transmits light of green (G), among the color filters 235. A curve 2503 indicates the transmittance of the color filter B, which transmits light of blue (B), among the color filters 235. A curve 2504 indicates the transmittance of the Fabry-Perot filter 236.

With the above-described configuration, it is possible to generate signals having the spectral characteristics of the color filter 235 on the first substrate 231 and to generate signals having the spectral characteristics of the Fabry-Perot filter 236 on the second substrate 232 simultaneously.

FIG. 26 is a graph showing angle dependence of a conventional Fabry-Perot filter. The horizontal axis of the graph indicates wavelength (nm). The vertical axis of the graph indicates transmittance. A curve 2601 indicates the transmittance of the Fabry-Perot filter in a case where the incidence angle is 30°. A curve 2602 indicates the transmittance of the Fabry-Perot filter in a case where the incidence angle is 15°. A curve 2603 indicates the transmittance of the Fabry-Perot filter in a case where the incidence angle is 0°. As shown in the drawing, in the Fabry-Perot filter, if the incidence angle of light becomes larger, the center wavelength of the transmission band changes.

SUMMARY OF THE INVENTION

An image-capturing element according to a first aspect of the invention includes a first substrate, a plurality of first pixels disposed in a matrix on the first substrate, each of the first pixels having a first light receiving element, a second substrate disposed at a position overlapping the first substrate and on a side opposite to a light receiving surface side of the first substrate when viewed from the light receiving surface side of the first substrate, a plurality of second pixels disposed in a matrix on the second substrate, each of the second pixels having a second light receiving element and a Fabry-Perot filter disposed on a light receiving surface side of the second light receiving element, and a plurality of optical systems disposed corresponding to the plurality of second pixels between the first substrate and the plurality of second pixels, the optical systems having negative refractive power.

According to a second aspect of the invention, in the first aspect, a plurality of first microlenses respectively disposed on the light receiving surface side of the plurality of first pixels may be provided.

According to a third aspect of the invention, in the first aspect, the plurality of optical systems may be disposed on a surface opposite to the light receiving surface side of the first substrate.

According to a fourth aspect of the invention, in the first aspect, each of the plurality of optical systems may have a recess with the light receiving surface side as an upper surface.

According to a fifth aspect of the invention, in the first aspect, the plurality of optical systems may be microlenses.

According to a sixth aspect of the invention, in the first aspect, each of the Fabry-Perot filters may have any transmission band from a plurality of kinds of transmission bands.

According to a seventh aspect of the invention, in the first aspect, the plurality of optical systems may be intralayer lenses.

According to an eighth aspect of the invention, in the first aspect, among the plurality of optical systems, the closer the optical system is disposed to the center of the first substrate, the smaller the refractive power may become, and the closer the optical system is disposed to the periphery of the first substrate, the larger the refractive power may become.

According to a ninth aspect of the invention, in the first aspect, among the plurality of optical systems, the closer the optical system is disposed to an optical axis of an imaging optical system, the smaller the refractive power may become, and the further the optical system is disposed from the optical axis of the imaging optical system, the larger the refractive power may become.

According to a tenth aspect of the invention, in the first aspect, each of the first pixels may have a color filter disposed on a light receiving surface side of the first light receiving element, the color filters may be disposed in a Bayer array, and the plurality of second pixels and the plurality of optical systems may be disposed so as to overlap the color filters which transmit blue light when viewed from the light receiving surface side of the first substrate.

According to an eleventh aspect of the invention, in the first aspect, each of the first pixels may have a color filter disposed on a light receiving surface side of the first light receiving element, the color filters may be disposed in a Bayer array, a part of the first pixels in which color filters transmitting green light are disposed may be provided as through holes, and the plurality of second pixels and the plurality of optical systems may be disposed so as to overlap the through holes when viewed from the light receiving surface side of the first substrate.

According to a twelfth aspect of the invention, in the first aspect, each of the first pixels may have a color filter disposed on a light receiving surface side of the first light receiving element, the color filters may be disposed in a Bayer array, a part of the color filters which transmit green light may be removed, and the plurality of second pixels and the plurality of optical systems may be disposed so as to overlap the first pixels with the color filters removed when viewed from the light receiving surface side of the first substrate.

According to a thirteenth aspect of the invention, in the first aspect, the first substrate, the plurality of first pixels, the second substrate, the plurality of second pixels, and the plurality of optical systems may be disposed at the tip of an endoscope.

DETAILED DESCRIPTION OF THE INVENTION

First Embodiment

Figure 1:
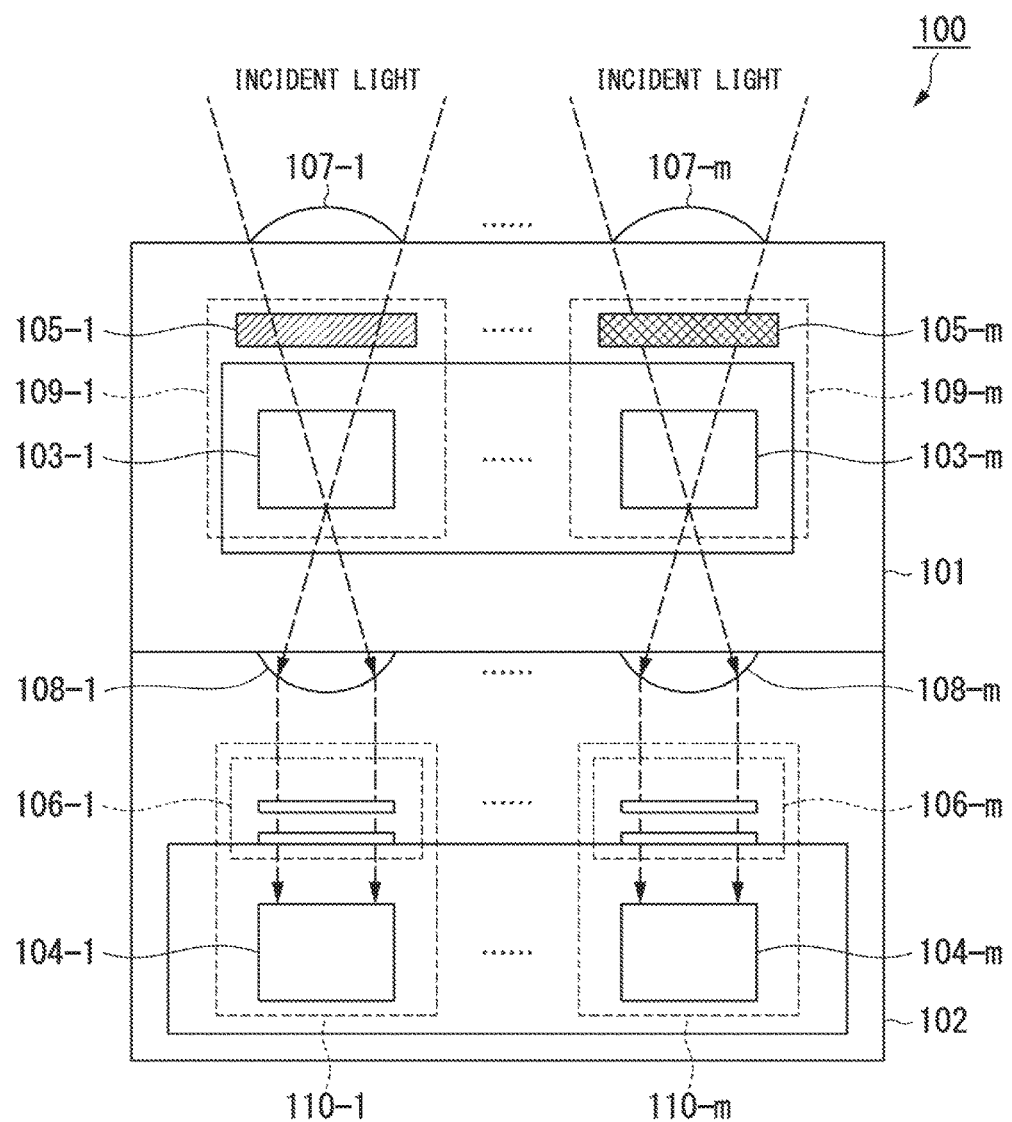
FIG. 1 is a sectional view showing a section of an image-capturing element in a first embodiment of the invention.

Hereinafter, a first embodiment of the invention will be described referring to the drawings. First, the configuration of an image-capturing element 100 will be described. FIG. 1 is a sectional view showing the section of the image-capturing element 100 in this embodiment. In the example shown in the drawing, the image-capturing element 100 includes a first substrate 101, a second substrate 102, first photodiodes 103-1 to 103-$m$ (first light receiving elements), second photodiodes 104-1 to 104-$m$ (second light receiving elements), color filters 105-1 to 105-$m$, Fabry-Perot filters 106-1 to 106-$m$, first microlenses 107-1 to 107-$m$, and second microlenses 108-1 to 108-$m$ (optical systems). A side which is irradiated with incident light is referred to as a light receiving surface. In this embodiment, an upper surface (an upper side of the paper surface of FIG. 1) of the first substrate 101 is a light receiving surface.

The first photodiodes 103-1 to 103-$m$ are disposed inside the first substrate 101. The color filters 105-1 to 105-$m$ are disposed on the light receiving surface side of the first photodiodes 103-1 to 103-$m$. Sets of the first photodiodes 103-1 to 103-$m$ and the color filters 105-1 to 105-$m$ are referred to as first pixels 109-1 to 109-$m$. For example, a set of the first photodiode 103-1 and the color filter 105-1 is referred to as the first pixel 109-1.

The second photodiodes 104-1 to 104-$m$ are disposed inside the second substrate 102. The Fabry-Perot filters 106-1 to 106-$m$ are disposed on the light receiving surface side of the second photodiodes 104-1 to 104-$m$. Sets of the second photodiodes 104-1 to 104-$m$ and the Fabry-Perot filters 106-1 to 106-$m$ are referred to as second pixels 110-1 to 110-$m$. For example, a set of the second photodiode 104-1 and the Fabry-Perot filter 106-1 is referred to as the second pixel 110-1.

The first microlenses 107-1 to 107-$m$ are disposed corresponding to the first pixels 109-1 to 109-$m$ and are disposed on the light receiving surface side of the first substrate 101. For example, the first microlens 107-1 is disposed on the light receiving surface side of the first substrate 101 and corresponds to the first pixel 109-1. The second microlenses 108-1 to 108-$m$ are disposed corresponding to the second pixels 110-1 to 110-$m$ between the first substrate 101 and the second pixels 110-1 to 110-$m$. For example, the second microlens 108-1 is disposed corresponding to the second pixel 110-1 between the first substrate 101 and the second pixel 110-1.

The first substrate 101 and the second substrate 102 are silicon substrates. The first substrate 101 transmits part of light incident thereon. The first photodiodes 103-1 to 103-$m$ output first signals according to the exposure. The second photodiodes 104-1 to 104-$m$ output second signals according to the exposure.

Each of the color filters 105-1 to 105-$m$ is one of a color filter R which transmits red (R) light, a color filter G which transmits green (G) light, and a color filter B which transmits blue (B) light. The arrangement of the color filters 105-1 to 105-$m$ will be described below.

The Fabry-Perot filters 106-1 to 106-$m$ transmit light of a predetermined narrow band. In this embodiment, the Fabry-Perot filters 106-1 to 106-$m$ transmit light of a narrow band centering on 830 nm. The Fabry-Perot filters 106-1 to 106-$m$ which transmit light of a narrow band centering on 830 nm are referred to as Fabry-Perot filters F.

The first microlenses 107-1 to 107-$m$ condense incident light. The first pixels 109-1 to 109-$m$ corresponding to the first microlenses 107-1 to 107-$m$ are irradiated with condensed light. The second microlenses 108-1 to 108-$m$ are microlenses having negative refractive power. In this embodiment, as an optical system having negative refractive power, a microlens which has a recess with a light receiving surface side as an upper surface is used. An optical system may have negative refractive power, and the shape thereof is not limited to a recess.

The second microlenses 108-1 to 108-$m$ substantially collimate light transmitted through the first pixels 109-1 to 109-$m$. That is, the second microlenses 108-1 to 108-$m$ refract light transmitted through the first pixels 109-1 to 109-$m$ such that the light receiving surfaces of the second pixels 110-1 to 110-$m$ corresponding to the second microlenses 108-1 to 108-$m$ are irradiated vertically with light transmitted through the first pixels 109-1 to 109-$m$.

Figure 2:
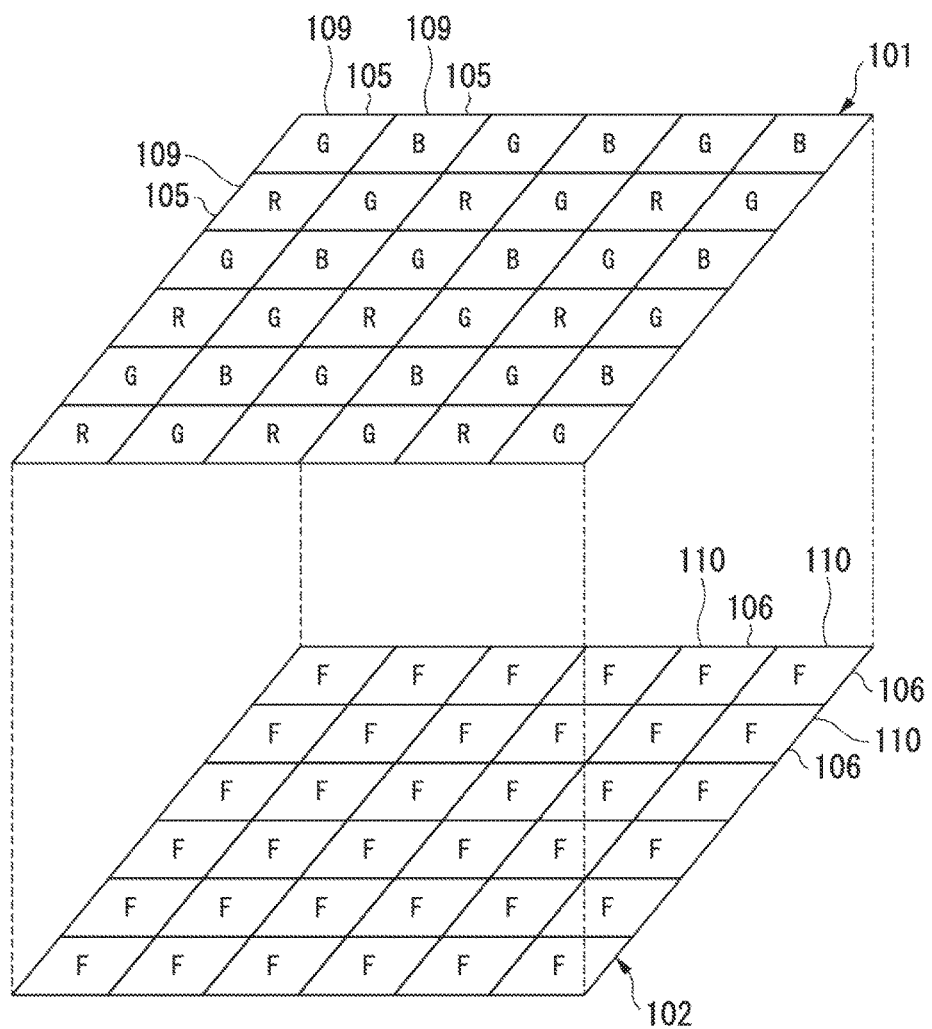
FIG. 2 is a schematic view showing the arrangement of color filters and the arrangement of Fabry-Perot filters in the first embodiment of the invention.

Next, the arrangement of the color filters 105 and the arrangement of the Fabry-Perot filters 106 will be described. FIG. 2 is a schematic view showing the arrangement of the color filters 105 and the arrangement of the Fabry-Perot filters 106 in this embodiment. In the example shown in FIG. 2, the first substrate 101 includes 36 first pixels 109 in total regularly arranged in a two-dimensional manner of six rows and six columns. The second substrate 102 includes 36 second pixels 110 in total regularly arranged in a two-dimensional manner of six rows and six columns. The number and arrangement of first pixels 109 included in the first substrate 101 and the number and arrangement of second pixels 110 included in the second substrate 102 are not limited to the example shown in FIG. 2, and any number and arrangement may be applied.

As shown in FIG. 2, the color filters 105 (color filters R, color filters G, and color filters B) are arranged in a Bayer array on the first substrate 101. The same Fabry-Perot filters 106 (Fabry-Perot filters F) are arranged on the second substrate 102.

Figure 3:
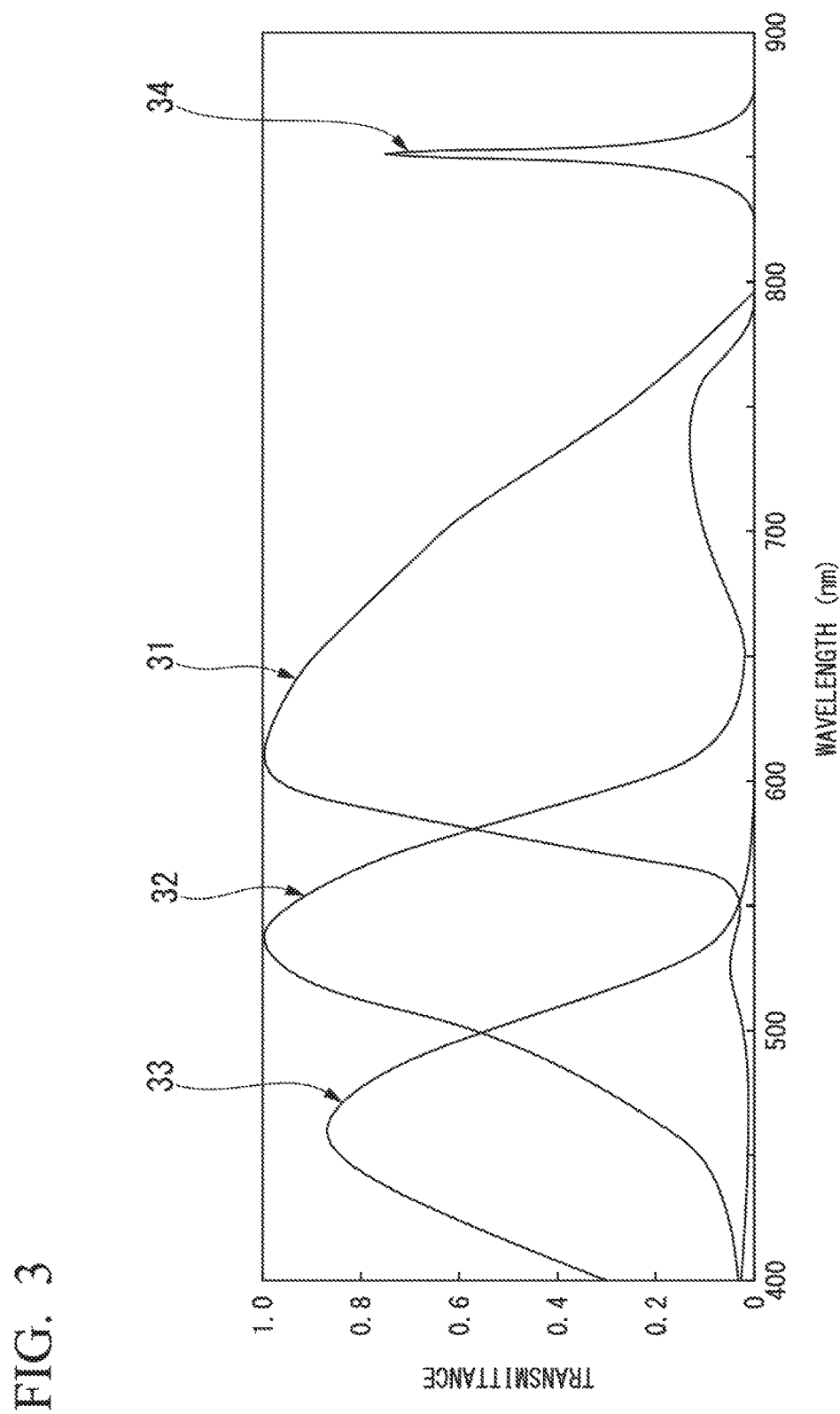
FIG. 3 is a graph showing the spectral characteristics of color filters and a Fabry-Perot filter in the first embodiment of the invention.

Next, the spectral characteristics of the color filters 105 and the Fabry-Perot filter 106 will be described. FIG. 3 is a graph showing the spectral characteristics of the color filters 105 and the Fabry-Perot filter 106 in this embodiment. The horizontal axis of the graph indicates wavelength (nm). The vertical axis of the graph indicates transmittance. A curve 31 indicates the transmittance of the color filter R, which transmits red (R) light, among the color filters 105. A curve 32 indicates the transmittance of the color filter G, which transmits green (G) light, among the color filters 105. A curve 33 indicates the transmittance of the color filter B, which transmits blue (B) light, among the color filters 105. A curve 34 indicates the transmittance of the Fabry-Perot filter 106.

As shown in FIG. 3, the color filter R most transmits light having a wavelength of 610 nm. The color filter G transmits light of a band centering on 540 nm. The color filter B transmits light of a band centering on 460 nm. The Fabry-Perot filter 106 transmits light of a narrow band centering on 830 nm.

Figure 4:
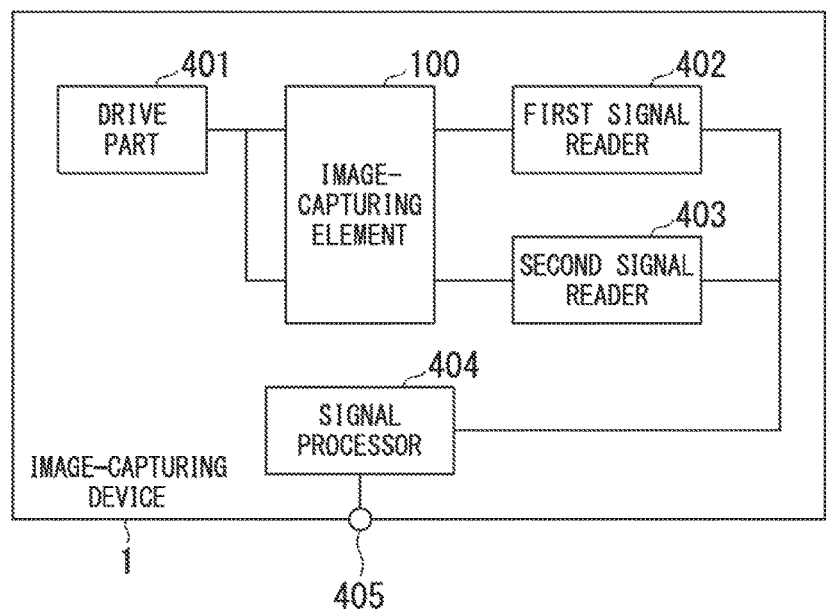
FIG. 4 is a block diagram showing the configuration of the image-capturing device in the first embodiment of the invention.

Next, the configuration of an image-capturing device 1 will be described. FIG. 4 is a block diagram showing the configuration of the image-capturing device 1 in this embodiment. The image-capturing device 1 includes a drive part 401, an image-capturing element 100, a first signal reader 402, a second signal reader 403, a signal processor 404, and a signal output terminal 405. The drive part 401 drives the image-capturing element 100, the first signal reader 402, and the second signal reader 403. The first signal reader 402 reads first pixel signals generated by the first pixels 109 of the image-capturing element 100 and outputs the first pixel signals to the signal processor 404. The second signal reader 403 reads second pixel signals generated by the second pixels 110 of the image-capturing element 100 and outputs the second pixel signals to the signal processor 404.

The signal processor 404 generates a first image based on the first pixel signals input from the first signal reader 402. The first pixel signals are an R signal according to the intensity of red light, a G signal according to the intensity of green light, and a B signal according to the intensity of blue light. That is, the first pixel signals are an RGB signal. Accordingly, the first image generated by the signal processor 404 is an RGB image. The signal processor 404 generates a second image based on the second pixel signal input from the second signal reader 403. The second pixel signals are fluorescent signals according to the intensity of light of a narrow band centering on 830 nm. Accordingly, the second image generated by the signal processor 404 is a fluorescent image. The signal processor 404 outputs the generated first image and second image from the signal output terminal 405.

Figure 5:
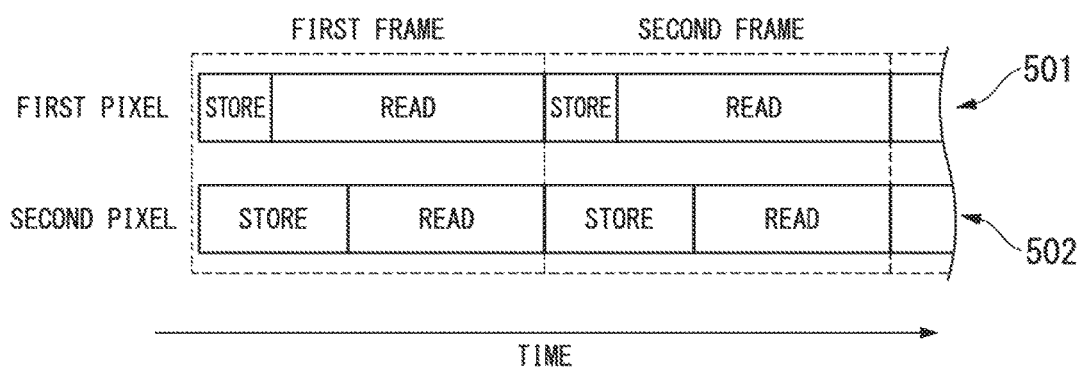
FIG. 5 is a timing chart showing the drive timing of the image-capturing device in the first embodiment of the invention.

Next, a drive method of the image-capturing device 1 will be described. FIG. 5 is a timing chart showing the drive timing of the image-capturing device 1 in this embodiment. In the example shown in FIG. 5, a timing chart 501 showing the drive timing of the first pixels 109 and a timing chart 502 showing the drive timing of the second pixels 110 are shown. The horizontal axis of the timing chart is time.

As shown in FIG. 5, in this embodiment, the charge storage time (exposure time) of the first pixels 109 is longer than the charge storage time (exposure time) of the second pixels 110. This is because the second pixels 110 are irradiated only with light transmitted through the first pixels 109, and accordingly, the amount of light with which the second pixels 110 is irradiated is smaller than the amount of light with which the first pixels 109 is irradiated. Furthermore, the reason is that the band of light detected by the second pixels 110 with the Fabry-Perot filters 106 is narrow and sensitivity is low compared to the first pixels 109 with the color filters 105. In this embodiment, the read time which is the time required for reading a signal from each pixel is set such that the RGB image and the fluorescent image have the same frame rate.

Figure 6:
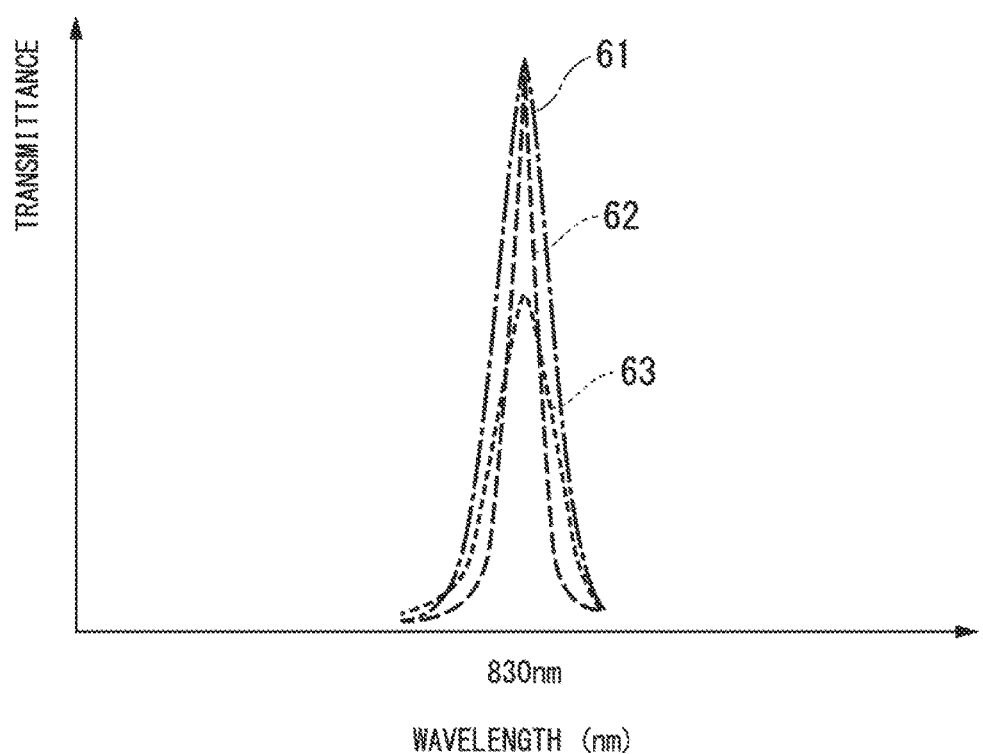
FIG. 6 is a graph showing the transmittance of a Fabry-Perot filter in a case where an incidence angle of light with which a first substrate is irradiated is changed in the first embodiment of the invention.

Next, the transmittance of the Fabry-Perot filter 106 in a case where the incidence angle of light with which the first substrate 101 is irradiated is changed will be described. FIG. 6 is a graph showing the transmittance of the Fabry-Perot filter 106 in a case where the incidence angle of light with which the first substrate 101 is irradiated is changed in this embodiment. The horizontal axis of the graph indicates wavelength (nm). The vertical axis of the graph indicates transmittance.

A curve 61 indicates the transmittance of the Fabry-Perot filter 106 in a case where the incidence angle of light with which the first substrate 101 is irradiated is 0°. A curve 62 indicates the transmittance of the Fabry-Perot filter 106 in a case where the incidence angle of light with which the first substrate 101 is irradiated is 15°. A curve 63 indicates the transmittance of the Fabry-Perot filter 106 in a case where the incidence angle of light with which the first substrate 101 is irradiated is 30°. As shown in FIG. 6, even if the incidence angle of light with which the fast substrate 101 is irradiated is changed, the center wavelength of the transmission band of the Fabry-Perot filter 106 is maintained at 830 nm.

In this embodiment, the second microlenses 108 substantially collimate light transmitted through the first pixels 109. That is, the second microlenses 108 refract light transmitted through the first pixels 109 such that the light receiving surfaces of the second pixels 110 corresponding to the second microlenses 108 are irradiated vertically with light transmitted through the first pixels 109 corresponding to the second microlens 108. Accordingly, as shown in FIG. 6, even in a case where the incidence angle of light with which the first substrate 101 is irradiated is changed, the center wavelength of the transmission band of the Fabry-Perot filter 106 is maintained at 830 nm.

As described above, according to this embodiment, the first substrate 101 and the second substrate 102 are laminated. The second substrate 102 is disposed at a position overlapping the first substrate 101 and on a side opposite to the light receiving surface side of the first substrate 101 when viewed from the light receiving surface side of the first substrate 101. The first substrate 101 transmits light. The second substrate 102 is irradiated with light transmitted through the first substrate 101.

With this, the first pixels 109 of the first substrate 101 and the second pixels 110 of the second substrate 102 can be simultaneously exposed. That is, the generation of the first signals with the first pixels 109 and the generation of the second signals with the second pixels 110 can be simultaneously performed. Accordingly, the signal processor 404 can simultaneously generate a first image based on the first signals and a second image based on the second signals.

According to this embodiment, the second microlenses 108 are disposed between the first substrate 101 and the second pixels 110 corresponding to the second pixels 110. The second microlenses 108 substantially collimate light transmitted through the first pixels 109. That is, the second microlenses 108 refract light transmitted through the first pixels 109 such that the light receiving surfaces of the second pixels 110 corresponding to the second microlenses 108 are irradiated vertically with light transmitted through the first pixels 109.

With this, even if the incidence angle of light with which the first substrate 101 is irradiated is any of 0°, 15°, 30°, or the like, the light receiving surfaces of the second pixels 110 are irradiated vertically with light transmitted through the first pixels 109. Accordingly, even if the incidence angle of light with which the first substrate 101 is irradiated is changed, the center wavelength of the transmission band of the Fabry-Perot filter 106 is maintained at 830 nm. Therefore, the image-capturing device 1 can capture the second image (fluorescent image) corresponding to a wavelength of interest with high accuracy.

Second Embodiment

Next, a second embodiment of the invention will be described. An image-capturing element of this embodiment is different from the image-capturing element 100 of the first embodiment in that a plurality of kinds of Fabry-Perot filters are provided. Other configurations of the image-capturing device and the image-capturing element are the same as those in the first embodiment. The operations of the image-capturing device and the image-capturing element in this embodiment are the same as those in the first embodiment.

Figure 7:
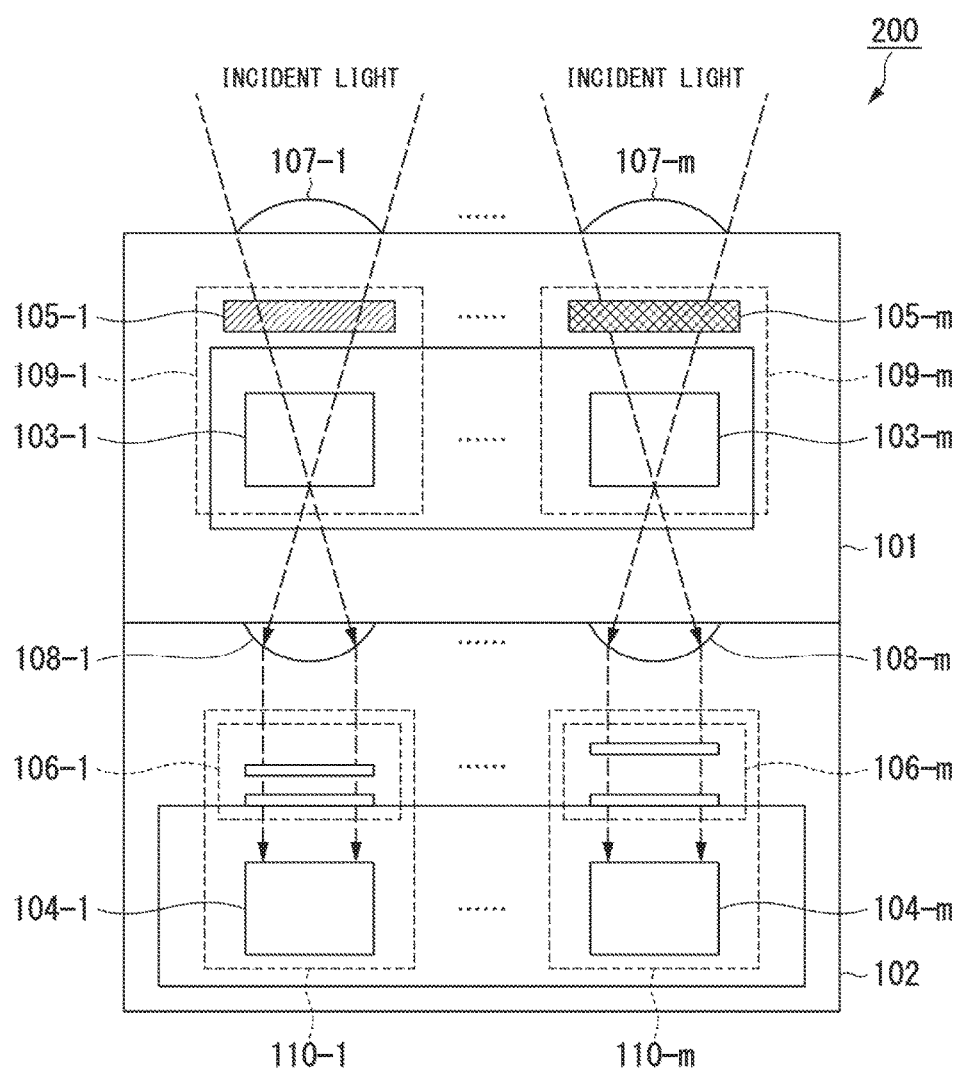
FIG. 7 is a sectional view showing a section of an image-capturing element in a second embodiment of the invention.

FIG. 7 is a sectional view showing a section of an image-capturing element 200 in this embodiment. In the example shown in FIG. 7, the image-capturing element 200 includes a first substrate 101, a second substrate 102, first photodiodes 103-1 to 103-$m$, second photodiodes 104-1 to 104-$m$, color filters 105-1 to 105-$m$, Fabry-Perot filters 106-1 to 106-$m$, first microlenses 107-1 to 107-$m$, and second microlenses 108-1 to 108-$m$.

The first substrate 101, the second substrate 102, the first photodiodes 103-1 to 103-$m$, the second photodiodes 104-1 to 104-$m$, the color filters 105-1 to 105-$m$, the first microlenses 107-1 to 107-$m$, and the second microlenses 108-1 to 108-$m$ are the same as those in the first embodiment.

The Fabry-Perot filters 106-1 to 106-$m$ transmit light of a predetermined narrow band. Each of the Fabry-Perot filters 106-1 to 106-$m$ is either a Fabry-Perot filter F1 which transmits light of a narrow band centering on 750 nm or a Fabry-Perot filter F2 which transmits light of a narrow band centering on 830 nm.

Figure 8:
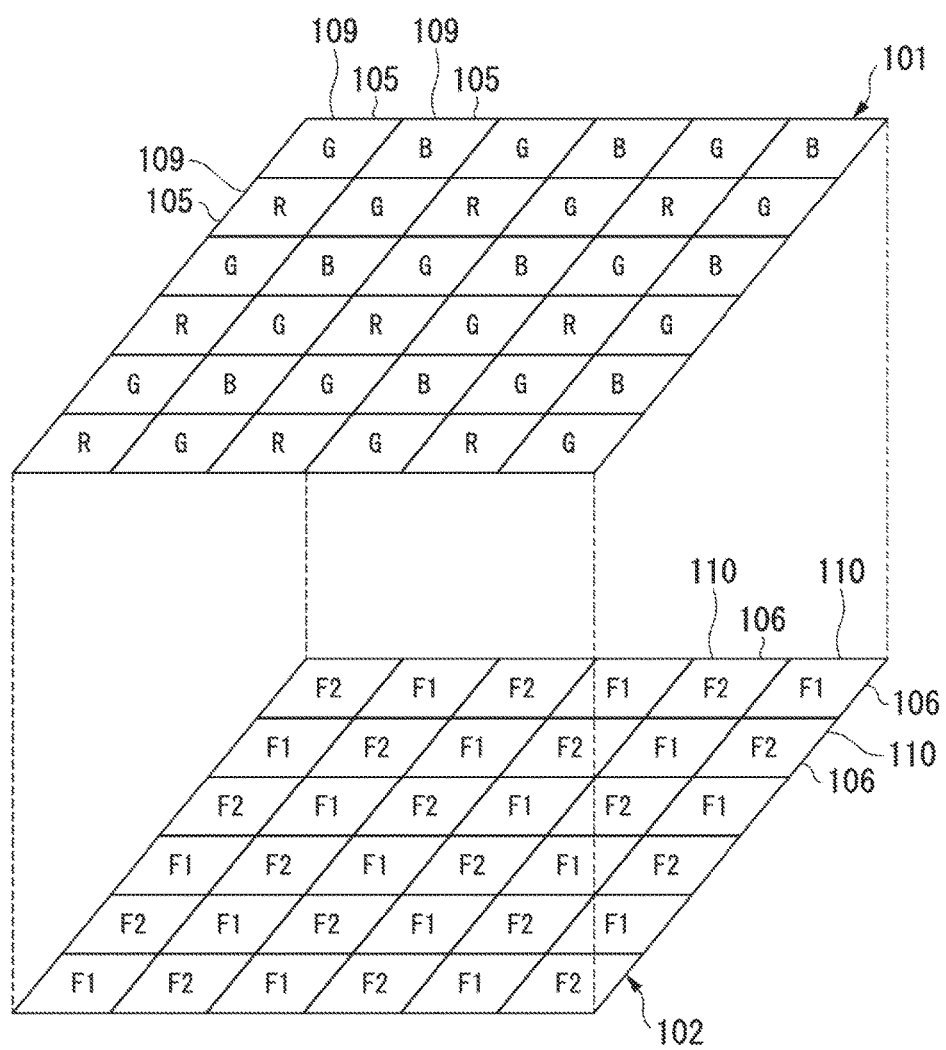
FIG. 8 is a schematic view showing the arrangement of color filters and the arrangement of Fabry-Perot filters in the second embodiment of the invention.

Next, the arrangement of the color filters 105 and the arrangement of the Fabry-Perot filters 106 will be described. FIG. 8 is a schematic view showing the arrangement of the color filters 105 and the arrangement of the Fabry-Perot filters 106 in this embodiment. In the example shown in FIG. 8, the first substrate 101 includes 36 first pixels 109 in total regularly arranged in a two-dimensional manner of six rows and six columns. The second substrate 102 includes 36 second pixels 110 in total regularly arranged in a two-dimensional manner of six rows and six columns. The number and arrangement of the first pixels 109 included in the first substrate 101 and the second pixels 110 included in the second substrate 102 are not limited to the example shown in FIG. 8, and any number and arrangement may be applied.

As shown in FIG. 8, the color filters 105 (color filter R, color filter G, and color filter B) are arranged in a Bayer array on the first substrate 101. The same Fabry-Perot filters 106 (Fabry-Perot filter F1, Fabry-Perot filter F2) are arranged alternately so as not to be adjacent to one another on the second substrate 102.

Figure 9:
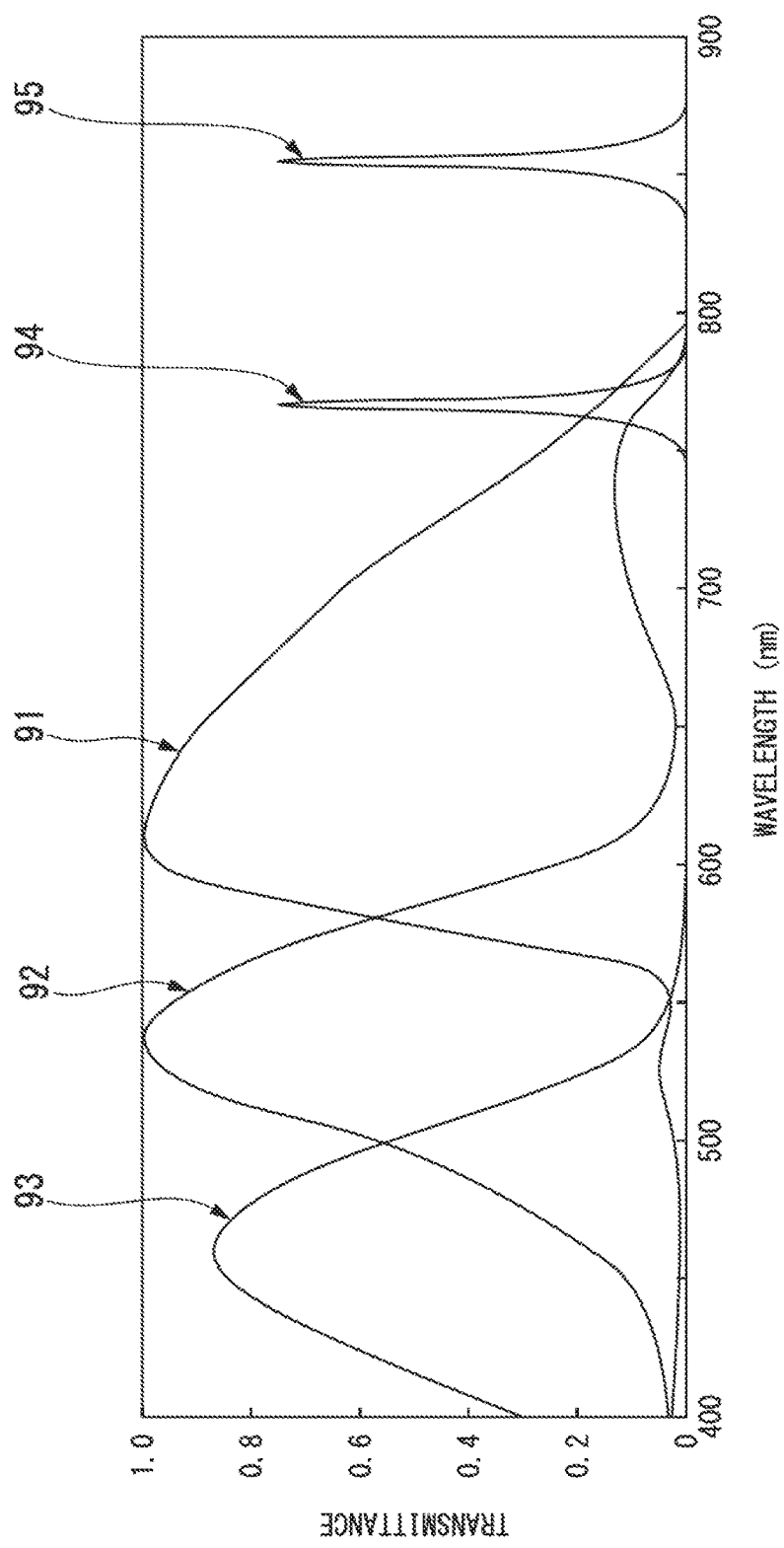
FIG. 9 is a graph showing the spectral characteristics of color filters and Fabry-Perot filters in the second embodiment of the invention.

Next, the spectral characteristics of the color filters 105 and the Fabry-Perot filters 106 will be described. FIG. 9 is a graph showing the spectral characteristics of the color filters 105 and the Fabry-Perot filters 106 in this embodiment. The horizontal axis of the graph indicates wavelength (nm). The vertical axis of the graph indicates transmittance.

A curve 91 indicates the transmittance of the color filter R, which transmits red (R) light, among the color filters 105. A curve 92 indicates the transmittance of the color filter G, which transmits green (G) light, among the color filters 105. A curve 93 indicates the transmittance of the color filter B, which transmits blue (B) light, among the color filters 105. A curve 94 indicates the transmittance of the Fabry-Perot filters F1, which transmits light of a narrow band centering on 750 nm, out of the Fabry-Perot filters 106. A curve 95 indicates the transmittance of the Fabry-Perot filter F2, which transmits light of a narrow band centering on 830 nm, out of the Fabry-Perot filters 106.

As described above, the image-capturing element 200 includes a plurality of kinds of Fabry-Perot filters 106 having different transmission bands. Accordingly, the second pixels 110 can generate the second signals according to the intensities of a plurality of kinds of wavelengths. Therefore, the signal processor 404 can generate a fluorescent image according to the intensities of a plurality of kinds of wavelengths.

Third Embodiment

Next, a third embodiment of the invention will be described. An image-capturing element of this embodiment is different from the image-capturing element 200 in the second embodiment in that intralayer lenses are used instead of the second microlenses 108-1 to 108-$m$. In this embodiment, in order to constitute the intralayer lenses, a wiring layer and protective layers are used. Other configurations of the image-capturing device and the image-capturing element are the same as those in the second embodiment. The operations of the image-capturing device and the image-capturing element in this embodiment are the same as those in the second embodiment.

Figure 10:
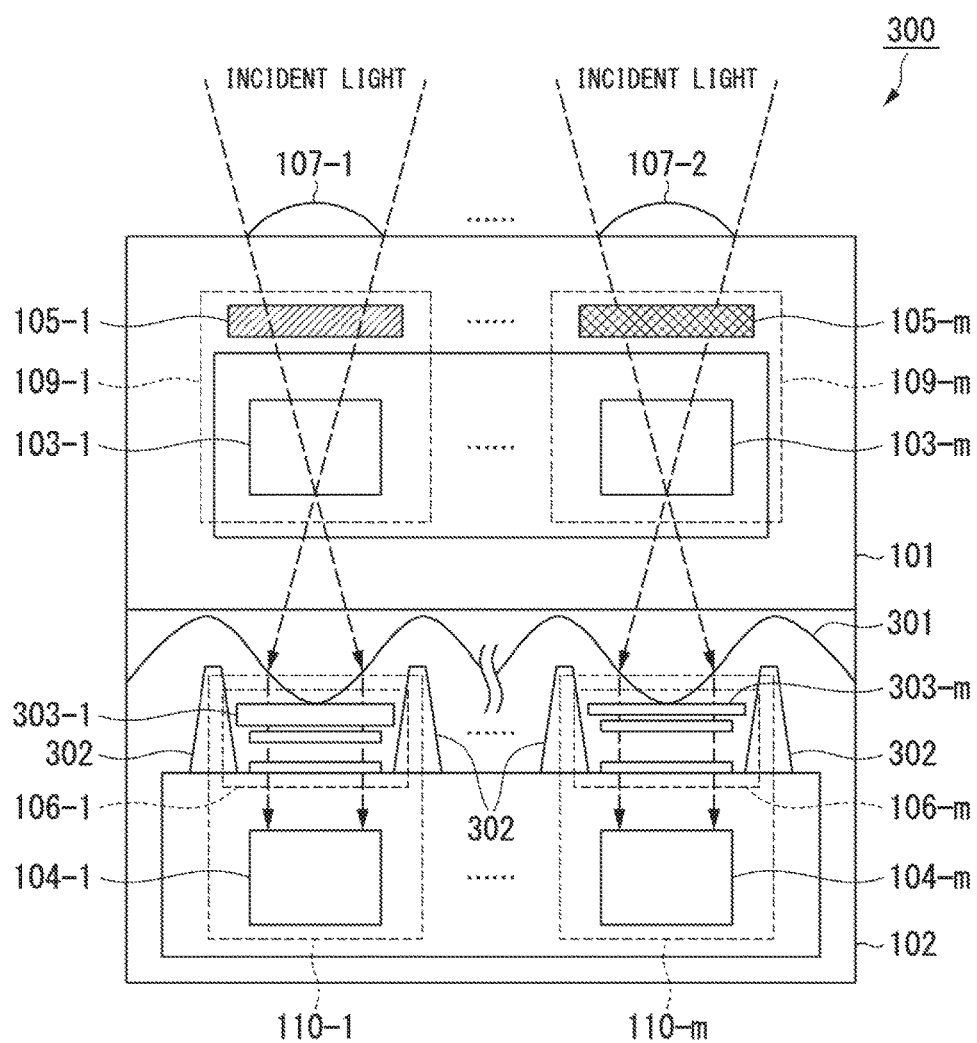
FIG. 10 is a sectional view showing a section of an image-capturing element in a third embodiment of the invention.

FIG. 10 is a sectional view showing a section of an image-capturing element 300 in this embodiment. In the example shown in FIG. 10, the image-capturing element 300 includes a first substrate 101, a second substrate 102, first photodiodes 103-1 to 103-$m$, second photodiodes 104-1 to 104-$m$, color filters 105-1 to 105-$m$, Fabry-Perot filters 106-1 to 106-$m$, first microlenses 107-1 to 107-$m$, an intralayer lens 301 (optical system), a wiring layer 302, and protective layers 303-1 to 303-$m$.

The first substrate 101, the second substrate 102, the first photodiodes 103-1 to 103-$m$, the second photodiodes 104-1 to 104-$m$, the color filters 105-1 to 105-$m$, the Fabry-Perot filters 106-1 to 106-$m$, and the first microlenses 107-1 to 107-$m$ are the same as those in the second embodiment.

The wiring layer 302 is a layer which is formed between the second pixels 110 of the second substrate 102. The wiring layer 302 blocks light such that other second pixels 110 are not irradiated with light with which the second pixel 110 is irradiated. The protective layers 303-1 to 303-$m$ are layers which are formed on the light receiving surface side of the Fabry-Perot filters 106-1 to 106-$m$. The protective layers 303-1 to 303-$m$ protect the Fabry-Perot filters 106-1 to 106-$m$. The protective layers 303-1 to 303-$m$ may be formed of any material as long as the material transmits light.

The intralayer lens 301 is a lens which is formed within the second substrate 102. For example, the intralayer lens 301 is formed by filling recess portions defined by the wiring layer 302 formed between the second pixel 110 and the protective layers 303-1 to 303-$m$ with a material transmitting light. The thickness of each of the protective layers 303-1 to 303-$m$ is set such that the distance between each second pixel 110 and the intralayer lens 301 is constant.

The intralayer lens 301 is a lens having negative refractive power. In this embodiment, as an optical system having negative refractive power, the recess portions with the light receiving surface side as an upper surface are provided. The intralayer lens 301 substantially collimates light transmitted through the first pixels 109-1 to 109-$m$. That is, the intralayer lens 301 refracts light transmitted through the first pixels 109-1 to 109-$m$ such that the light receiving surfaces of the second pixels 110-1 to 110-$m$ corresponding to the intralayer lens 301 are irradiated vertically with light transmitted through the first pixels 109-1 to 109-$m$.

As described above, in this embodiment, the intralayer lens 301 is used instead of the second microlenses 108. The intralayer lens 301 can be constituted within the second substrate 102. Therefore, it is possible to reduce the distance between the first substrate 101 and the second substrate 102, and to reduce the thickness of the image-capturing element 300.

Fourth Embodiment

Next, a fourth embodiment of the invention will be described. An image-capturing element in this embodiment is different from the image-capturing element 200 in the second embodiment in that the structure of the second microlens is different. Other configurations of the image-capturing device and the image-capturing element are the same as those in the second embodiment. The operations of the image-capturing device and the image-capturing element in this embodiment are the same as those in the second embodiment.

Figure 11:
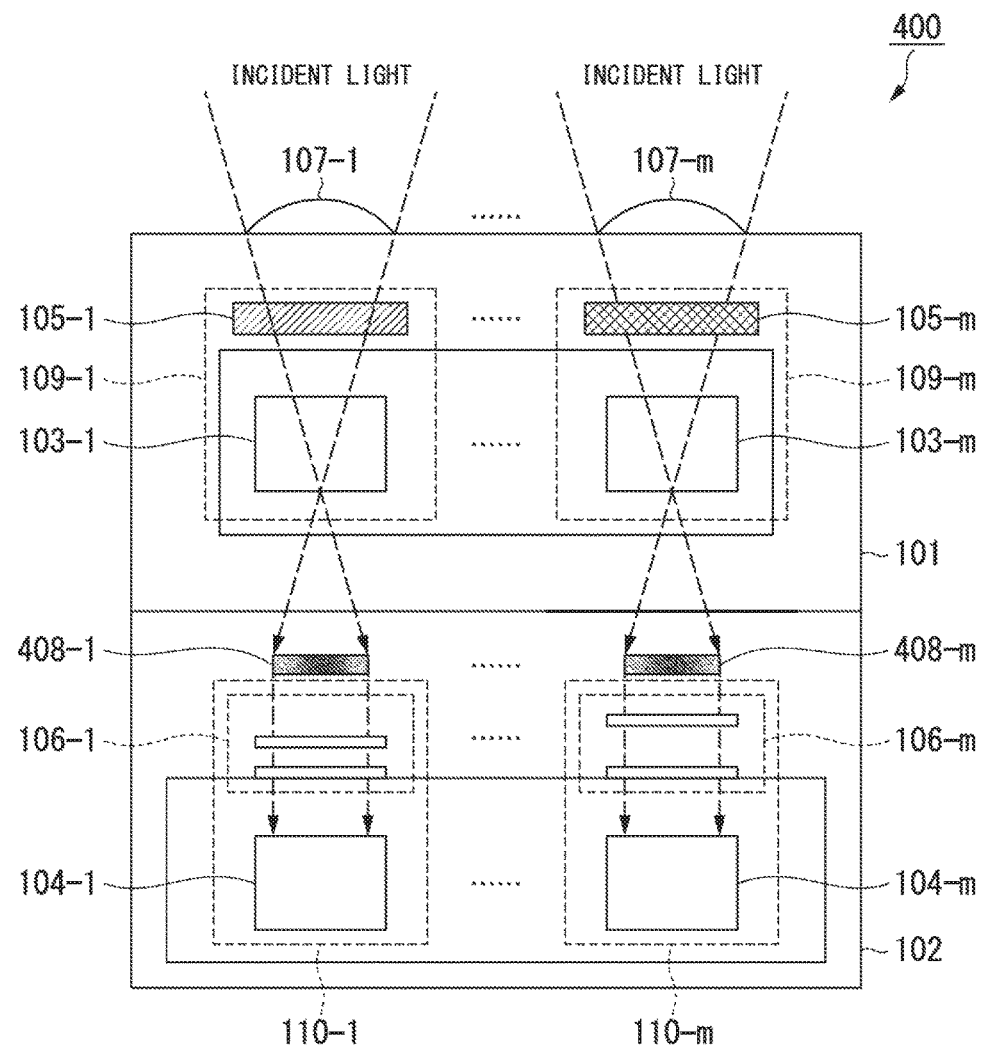
FIG. 11 is a sectional view showing a section of an image-capturing element in a fourth embodiment of the invention.

FIG. 11 is a sectional view showing a section of an image-capturing element 400 in this embodiment. In the example shown in FIG. 11, the image-capturing element 400 includes a first substrate 101, a second substrate 102, first photodiodes 103-1 to 103-$m$, second photodiodes 104-1 to 104-$m$, color filters 105-1 to 105-$m$, Fabry-Perot filters 106-1 to 106-$m$, first microlenses 107-1 to 107-$m$, and second microlenses 408-1 to 408-$m$.

The first substrate 101, the second substrate 102, the first photodiodes 103-1 to 103-$m$, the second photodiodes 104-1 to 104-$m$, the color filters 105-1 to 105-$m$, the Fabry-Perot filters 106-1 to 106-$m$, and the first microlenses 107-1 to 107-$m$ are the same as those in the second embodiment.

The second microlenses 408-1 to 408-$m$ are optical systems having negative refractive power. In this embodiment, the second microlenses 408-1 to 408-$m$ are optical systems which have a function of a microlens with the distribution of refractive indexes. The second microlenses 408-1 to 408-$m$ are formed of a material in which a refractive index is low at the center and becomes higher toward the periphery. Since the refractive index is changed depending on the materials, the shape of the second microlenses 408-1 to 408-$m$ is flat.

The second microlenses 408-1 to 408-$m$ change the refractive index according to the positions within the lenses, thereby having the same functions as the second microlenses 108-1 to 108-$m$ in the second embodiment. Specifically, the second microlenses 408-1 to 408-$m$ substantially collimate light transmitted through the first pixels 109-1 to 109-$m$. That is, the second microlenses 408-1 to 408-$m$ refract light transmitted through the first pixels 109-1 to 109-$m$ such that the light receiving surfaces of the second pixels 110-1 to 110-$m$ corresponding to the second microlenses 408-1 to 408-$m$ are irradiated vertically with light transmitted through the first pixels 109-1 to 109-$m$.

As described above, in this embodiment, the second microlenses 408-1 to 408-m which are optical systems having a function of a microlens are used. The shape of the second microlenses 408-1 to 408-m is flat. Therefore, it is possible to reduce the distance between the first substrate 101 and the second substrate 102, and to reduce the thickness of the image-capturing element 400.

Fifth Embodiment

Next, a fifth embodiment of the invention will be described. An image-capturing element of this embodiment is different from the image-capturing element 200 in the second embodiment in that a refractive index changes according to the arrangement of the second microlenses. Other configurations of the image-capturing device and the image-capturing element are the same as those in the second embodiment. The operations of the image-capturing device and the image-capturing element of this embodiment are the same as those in the second embodiment.

Figure 12:
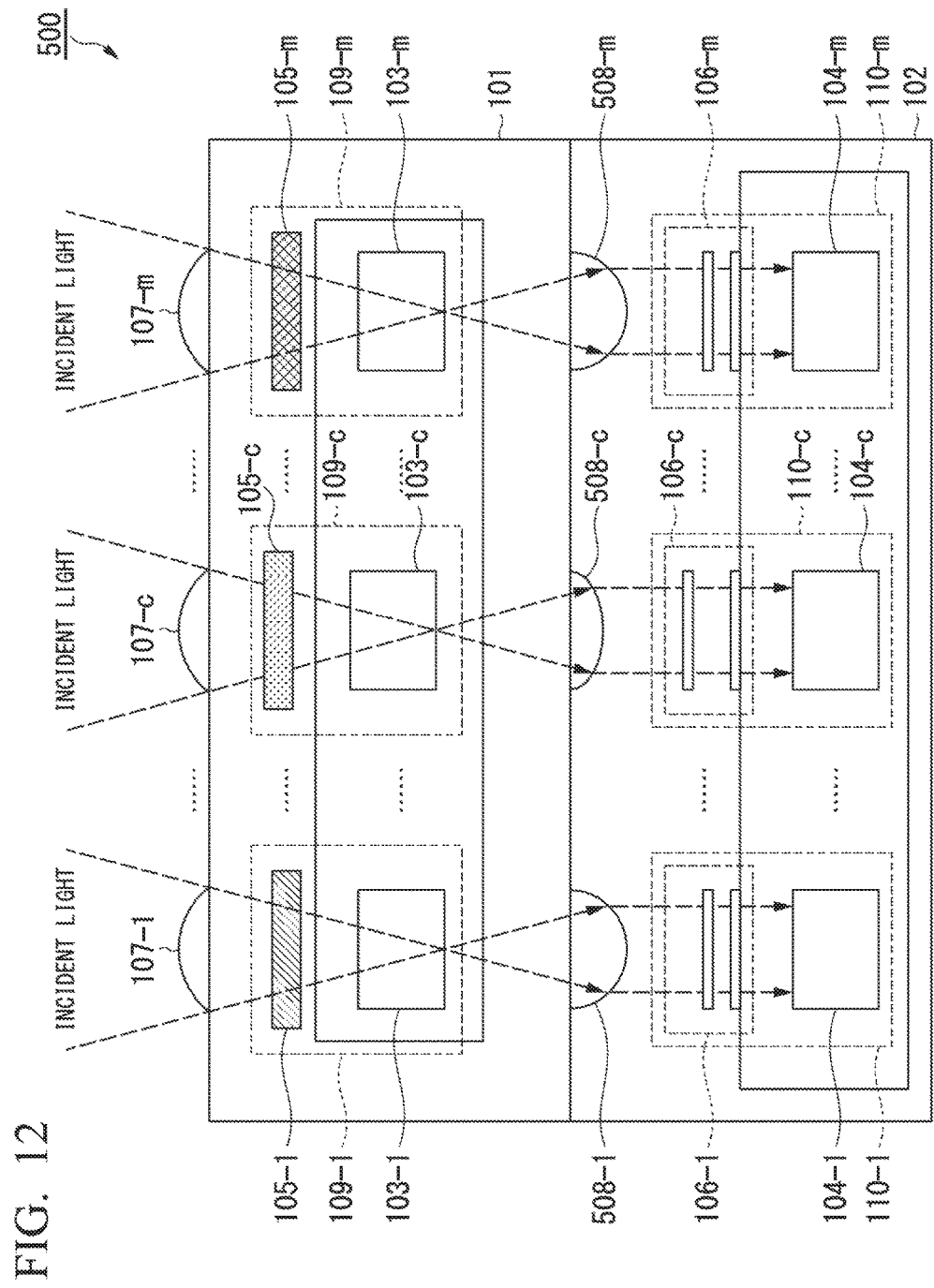
FIG. 12 is a sectional view showing a section of an image-capturing element in a fifth embodiment of the invention.

FIG. 12 is a sectional view showing a section of an image-capturing element 500 in this embodiment. In the example shown in FIG. 12, the image-capturing element 500 includes a first substrate 101, a second substrate 102, first photodiodes 103-1, . . . , 103-c, . . . , 103-m, second photodiodes 104-1, . . . , 104-c, . . . , 104-m, color filters 105-1, . . . , 105-c, . . . , 105-m, Fabry-Perot filters 106-1, . . . , 106-c, . . . , 106-m, first microlenses 107-1, . . . , 107-c, . . . , 107-m, and second microlenses 508-1, . . . , 508-c, . . . , 508-m.

The first substrate 101, the second substrate 102, the first photodiodes 103-1, . . . , 103-c, . . . , 103-m, the second photodiodes 104-1, . . . , 104-c, . . . , 104-m, the color filters 105-1, . . . , 105-c, . . . , 105-m, the Fabry-Perot filters 106-1, . . . , 106-c, . . . , 106-m, and the first microlenses 107-1, . . . , 107-c, . . . , 107-m are the same as those in the second embodiment.

The second microlenses 508-1 to 508-m are microlenses having negative refractive power. In this embodiment, the second microlenses 508-1 to 508-m have recess portions with the light receiving surface side as an upper surface. The second microlenses 508-1, . . . , 508-c, . . . , 508-m are different in refractive power according to the arrangement positions. Specifically, among the second microlenses 508 arranged in a two-dimensional manner, the closer the second microlens 508 is disposed to the center, the lower the refractive power becomes. Among the second microlenses 508 arranged in a two-dimensional manner, the closer the second microlens 508 is disposed to the outside, the higher the refractive index becomes.

In a case where the image-capturing element 500 is used in the image-capturing device 1, the optical axis of the imaging optical system of the image-capturing device 1 is the center among the second microlenses 508 arranged in a two-dimensional manner. Accordingly, when the optical axis of the imaging optical system is used as a reference, among the second microlenses 508 arranged in a two-dimensional manner, the closer the second microlens 508 is disposed to the optical axis of the imaging optical system, the lower the refractive power becomes. Among the second microlenses 508 arranged in a two-dimensional manner, the further the second microlens 508 is disposed from the optical axis of the imaging optical system, the higher the refractive power becomes.

In the example shown in FIG. 12, the second microlenses 508-1 and 508-m are disposed at positions closest to the outside. The second microlens 508-c is disposed at a position closest to the center. Accordingly, among the second microlenses 508-1 to 508-m, the second microlenses 508-1 and 503-m have the highest refractive power. Among the second microlenses 508-1 to 508-m, the second microlens 508-c has the lowest refractive power.

With this configuration, it is possible to cope with the change in the incidence angle of light in the image-capturing element 500, and to irradiate the light receiving surfaces of the second pixels 110-1, . . . , 110-c, . . . , 110-m more vertically with light. Therefore, the image-capturing device 1 including the image-capturing element 500 can capture the second image (fluorescent image) corresponding to a wavelength of interest with higher accuracy.

Sixth Embodiment

Next, a sixth embodiment of the invention will be described. An image-capturing element of this embodiment is different from the image-capturing element 200 in the second embodiment in that the second pixels are irradiated only with light transmitted through the first pixels 109 in which the color filter B transmitting blue light is disposed. Other configurations of the image-capturing device and the image-capturing element are the same as those in the second embodiment. The operations of the image-capturing device and the image-capturing element in this embodiment are the same as those in the second embodiment.

Figure 13:
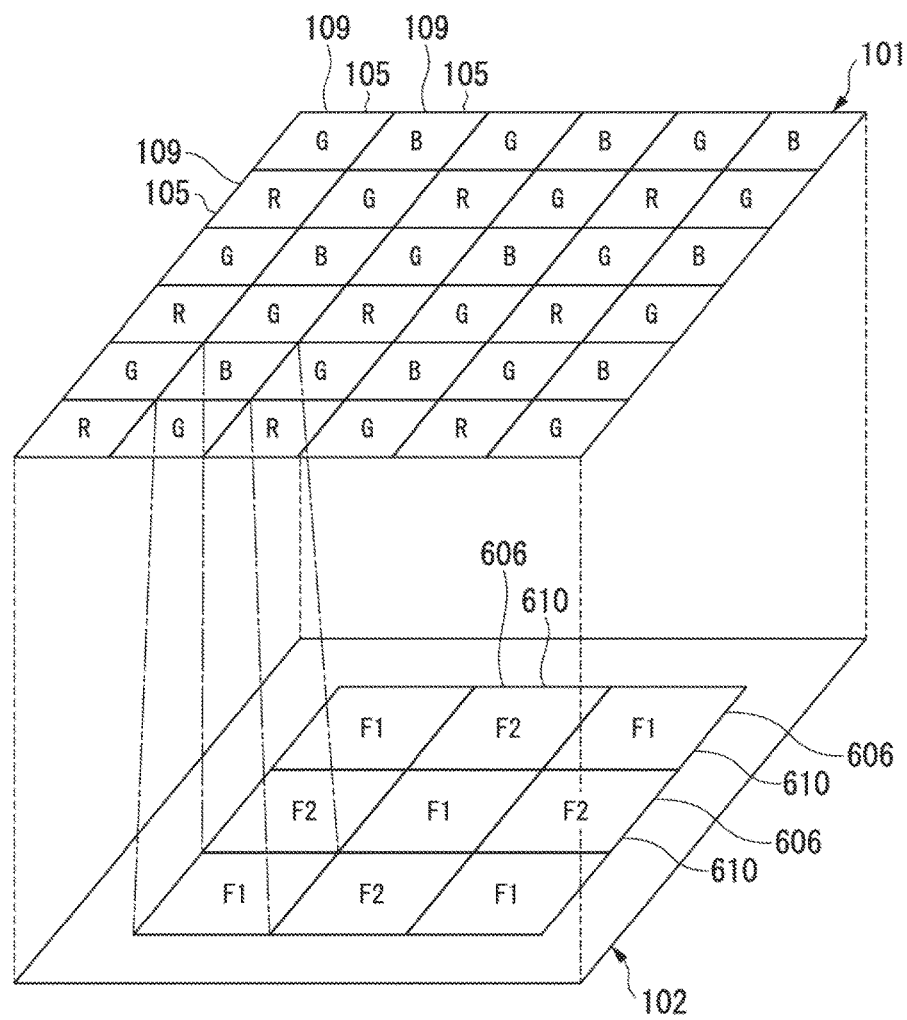
FIG. 13 is a schematic view showing the arrangement of first pixels with color filters and the arrangement of second pixels with Fabry-Perot filters in a sixth embodiment of the invention.

FIG. 13 is a schematic view showing the arrangement of first pixels 109 with a color filter 105 and second pixels 610 with a Fabry-Perot filter 606 in this embodiment. In the example shown in FIG. 13, the first substrate 101 includes 36 first pixels 109 in total regularly arranged in a two-dimensional manner of six rows and six columns. The second substrate 102 includes nine second pixels 610 regularly arranged in a two-dimensional manner of three rows and three columns.

In this embodiment, the second pixels 610 are irradiated only with light transmitted through the first pixels 109 in which the color filter B transmitting blue light is disposed. The number of first pixels 109 in which the color filter B is disposed is one fourth of all first pixels 109. Accordingly, the number of second pixels 610 corresponding to the first pixels 109 in which the color filter B is disposed is one fourth of the number of first pixels 109. Since the number of second pixels 610 is one fourth of the number of first pixels 109, the area of the second pixels 610 can be four times.

With this configuration, it is possible to allow the first pixels 109 in which the color filter B is disposed to correspond to the second pixels 610 one-to-one. The number and arrangement of the first pixels 109 included in the first substrate 101 and the second pixels 610 included in the second substrate 102 are not limited to the example shown in FIG. 13, and any number and arrangement may be applied.

As shown in FIG. 13, the color filters 105 (color filter R, color filter G, and color filter B) are arranged in a Bayer array on the first substrate 101. The same Fabry-Perot filters 606 (Fabry-Perot filter F1, Fabry-Perot filter F2) are arranged alternately so as not to be adjacent to one another on the second substrate 102.

Figure 14:
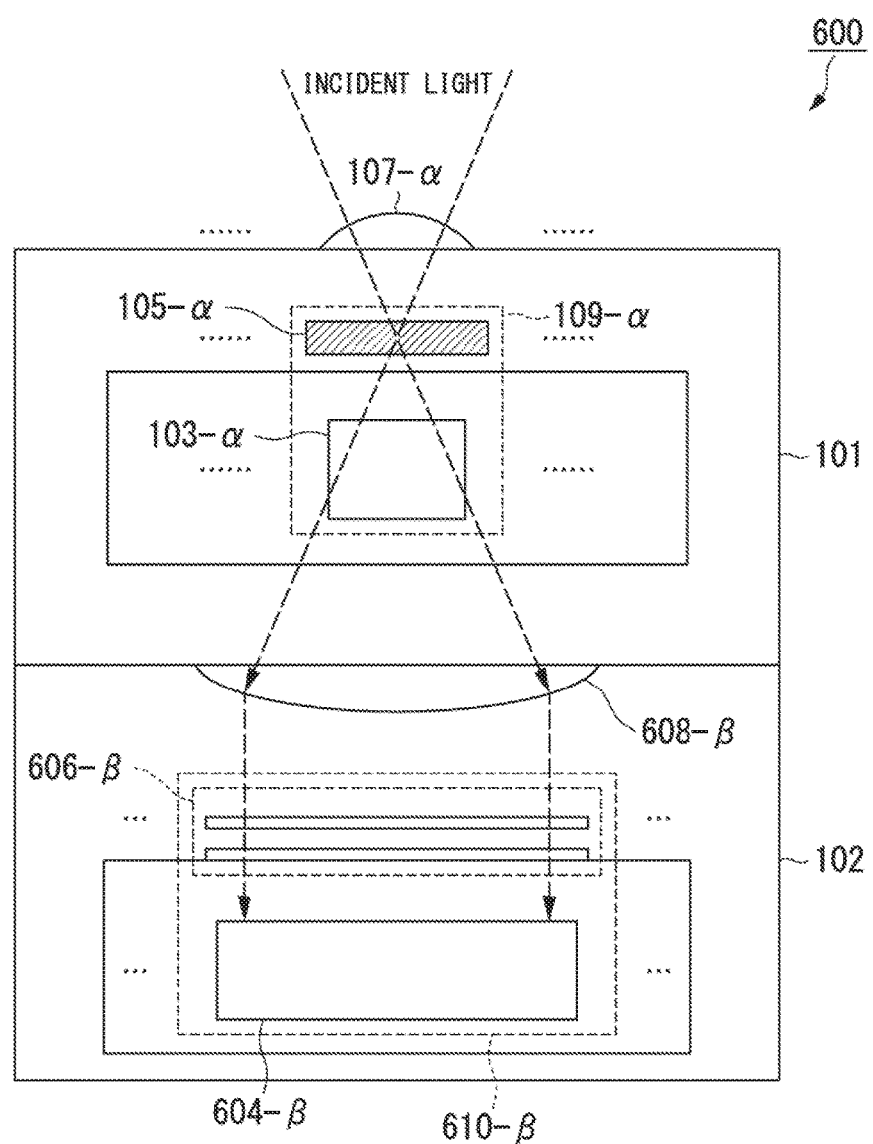
FIG. 14 is a sectional view showing a section of a place where a first pixel with a color filter B disposed therein is formed in the image-capturing element in the sixth embodiment of the invention.

FIG. 14 is a sectional view showing a section of a place where the first pixel 109 with the color filter B disposed is formed in the image-capturing element 600 in this embodiment. In the example shown in FIG. 14, the image-capturing element 600 includes a first substrate 101, a second substrate 102, a first photodiode 103-α, a second photodiode 604-β, a color filter 105-α, a Fabry-Perot filter 606-β, a first microlens 107-α, and a second microlens 608-β.

The first substrate 101, the second substrate 102, the first photodiode 103-α, and the first microlens 107-α are the same as those in the second embodiment. The area of the second photodiode 604-β is four times the area of the second photodiodes 104-1 to 104-m in the second embodiment. The area of the Fabry-Perot filter 606-β is four times the area of the Fabry-Perot filters 106-1 to 106-m in the second embodiment.

The second microlens 608-β is a microlens having negative refractive power. The second microlens 608-β causes the entire light receiving surface of the second pixel 610-β corresponding to the second microlens 608-β to be irradiated only with light transmitted through the first pixels 109, in which the color filter B transmitting blue light is disposed, among the first pixels 109-1 to 109-m. The second microlens 608-β substantially collimates light transmitted through the first pixels 109 in which the color filter B transmitting blue light is disposed. That is, the second microlens 608-β refracts light transmitted through the first pixels 109 such that the entire light receiving surface of the second pixel 610-β corresponding to the second microlens 608-β is irradiated only with light transmitted through the first pixels 109, in which the color filter B transmitting blue light is disposed, among the first pixels 109-1 to 109-m.

As described above, the second microlens 608 causes the entire light receiving surfaces of the second pixels 610 corresponding to the second microlens 608 to be irradiated vertically only with light transmitted through the first pixels 109, in which the color filter B transmitting blue light is disposed, among the first pixels 109. The color filter B which transmits blue light transmits more light. Furthermore, it is possible to increase the area of the second pixels 610. Accordingly, the second pixels 610 can receive more light. Therefore, since the Fabry-Perot filters 606 are provided, even in the second pixels 610 having a narrow band of light to be detected and low sensitivity, it is possible to output sufficient second signals.

Seventh Embodiment

Next, a seventh embodiment of the invention will be described. An image-capturing element of this embodiment is different from the image-capturing element 600 in the sixth embodiment in that a part of the first pixels 109, in which the color filter B transmitting blue light is disposed, among the first pixels 109 is changed to through holes. Other configurations of the image-capturing device and the image-capturing element are the same as those in the sixth embodiment. The operations of the image-capturing device and the image-capturing element in this embodiment are the same as those in the sixth embodiment.

Figure 15:
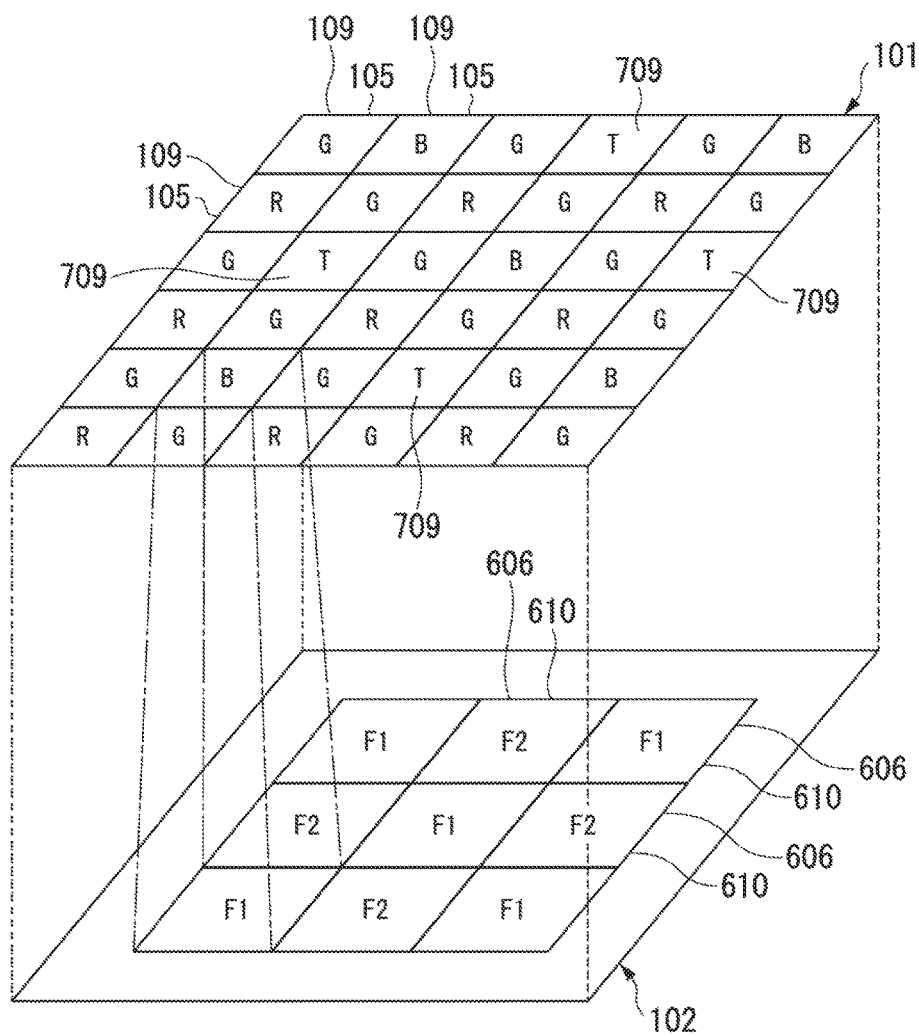
FIG. 15 is a schematic view showing the arrangement of first pixels with color filters and through holes and the arrangement of second pixels with Fabry-Perot filters in a seventh embodiment of the invention.

FIG. 15 is a schematic view showing the arrangement of first pixels 109 and through holes 709 with a color filter 105 and the arrangement of second pixels 610 with a Fabry-Perot filter 606 in this embodiment. In the example shown in FIG. 15, the first substrate 101 includes 32 first pixels 109 and four through holes 709 regularly arranged in a two-dimensional manner of six rows and six columns. The second substrate 102 includes nine second pixels 610 in total regularly arranged in a two-dimensional manner of three rows and three columns.

In this embodiment, the second pixels 610 are irradiated only with light transmitted through the first pixels 109 or the through holes 709 in which the color filter B transmitting blue light is disposed. With this configuration, it is possible to allow the first pixels 109 and the through holes 709, in which the color filter B is disposed, to correspond to the second pixels 610 one-to-one. The number and arrangement of the first pixels 109 and the through holes 709 included in the first substrate 101 and the second pixels 610 included in the second substrate 102 are not limited to the example shown in FIG. 15, and any number and arrangement may be applied.

As shown in FIG. 15, excluding the places where the through holes 709 are formed, the color filters 105 (color filter R, color filter G, and color filter B) are arranged in a Bayer array on the first substrate 101. The same Fabry-Perot filters 606 (Fabry-Perot filter F1, Fabry-Perot filter F2) are arranged alternately so as not to be adjacent to one another on the second substrate 102.

Figure 16:
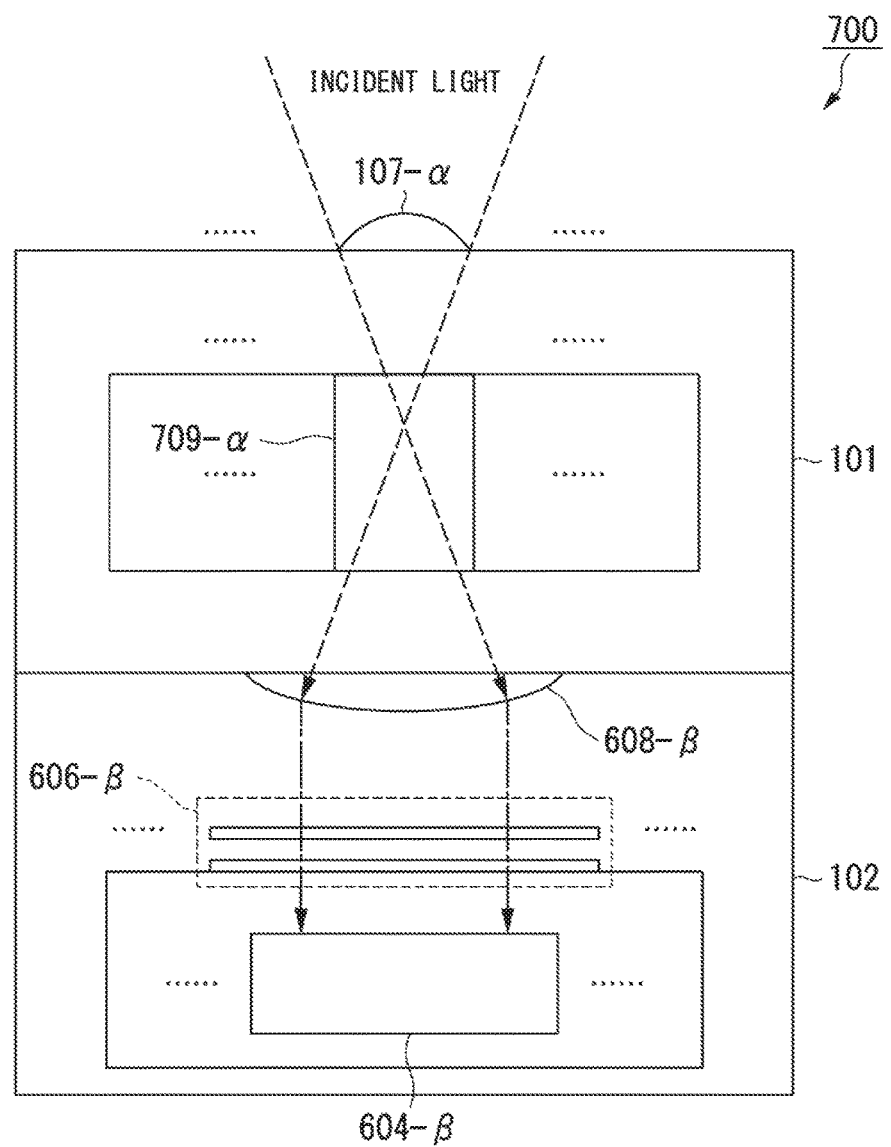
FIG. 16 is a sectional view showing a section of a place where a through hole is formed in the image-capturing element in the seventh embodiment of the invention.

FIG. 16 is a sectional view showing a section of a place where the through hole 709 is formed in the image-capturing element 700 of this embodiment. In the example shown in FIG. 16, the image-capturing element 700 includes a first substrate 101, a second substrate 102, a through hole 709-α, a second photodiode 604-β, a Fabry-Perot filter 606-β, a first microlens 107-α, and a second microlens 608-β.

The first substrate 101, the second substrate 102, the second photodiode 604-β, the Fabry-Perot filter 606-β, the first microlens 107-α, and the second microlens 608-β are the same as those in the sixth embodiment. The through hole 709 is, for example, a cavity. The through holes 709 transmit incident light directly without absorbing or reflecting light. The section of the place where the first pixel 109 with the color filter B disposed is formed is the same as in the sixth embodiment.

As described above, the second microlens 608 causes the entire light receiving surface of the second pixels 610 corresponding to the second microlens 608 to be irradiated vertically only with light transmitted through the first pixels 109 or the through holes 709, in which the color filter B transmitting blue light is disposed, among the first pixels 109. The color filter B which transmits blue light transmits more light. The through holes 709 transmit incident light directly. Furthermore, it is possible to increase the area of the second pixels 610. Accordingly, the second pixels 610 can receive more light. Therefore, since the Fabry-Perot filters 606 are provided, even in the second pixels 610 having a narrow band of light to be detected and low sensitivity, it is possible to output sufficient second signals.

Since the through holes 709 are provided, there is a region where the first pixel 109 is lacking; however, the signal processor 404 performs demosaic processing, thereby generating the first image based on the first signals.

Eighth Embodiment

Next, an eighth embodiment of the invention will be described. An image-capturing element in this embodiment is different from the image-capturing element 600 in the sixth embodiment in that a part of the first pixels 109 in which the color filter B transmitting blue light is disposed is changed to first pixels 809 in which a clear filter 805 is disposed. Other configurations of the image-capturing device and the image-capturing element are the same as those in the sixth embodiment. The operations of the image-capturing device and the image-capturing element in this embodiment are the same as those in the sixth embodiment.

Figure 17:
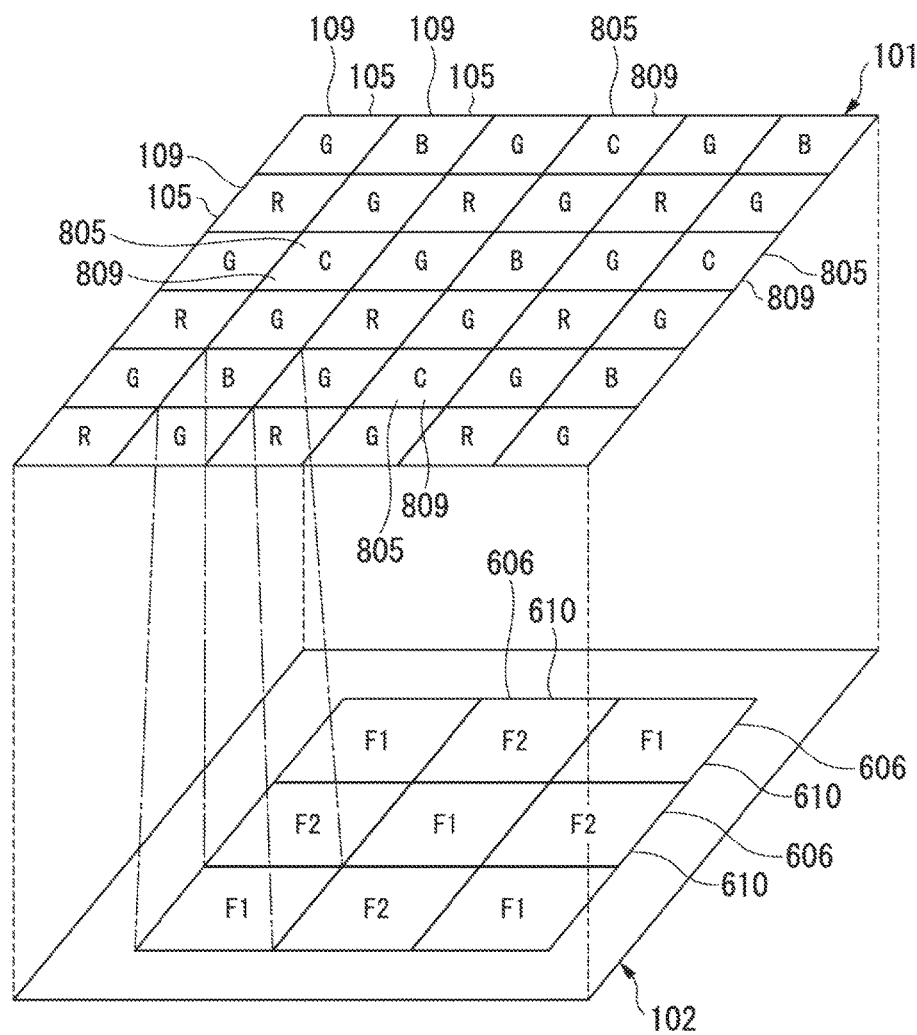
FIG. 17 is a schematic view showing the arrangement of first pixels with color filters and first pixels with clear filters disposed therein and the arrangement of second pixels with Fabry-Perot filters in an eighth embodiment of the invention.

FIG. 17 is a schematic view showing the arrangement of the first pixels 109 with the color filter 105 and the first pixels 809 with the clear filter 805 and the arrangement of the second pixels 610 with the Fabry-Perot filter 606 in this embodiment. In the example shown in FIG. 17, the first substrate 101 includes 32 first pixels 109 and four first pixels 809 regularly arranged in a two-dimensional manner of six rows and six columns. The second substrate 102 includes nine second pixels 610 in total regularly arranged in a two-dimensional manner of three rows and three columns.

In this embodiment, the second pixels 610 are irradiated only with light transmitted through the first pixels 109 in which the color filter B transmitting blue light is disposed or the first pixels 809 in which the clear filter 805 is disposed. With this configuration, it is possible to allow the first pixels 109, in which the color filter B is disposed, and the first pixels 809, in which the clear filter 805 is disposed, to correspond to the second pixels 610 one-to-one. The number and arrangement of the first pixels 109 and the first pixels 809 included in the first substrate 101 and the second pixels 610 included in the second substrate 102 are not limited to the example shown in FIG. 17, and any number and arrangement may be applied.

As shown in FIG. 17, excluding the places where the first pixels 809 with the clear filter 805 disposed are formed, the color filters 105 (color filter R, color filter G, and color filter B) are arranged in a Bayer array on the first substrate 101. The same Fabry-Perot filters 606 (Fabry-Perot filter F1, Fabry-Perot filter F2) are arranged alternately so as not to be adjacent to one another on the second substrate 102.

Figure 18:
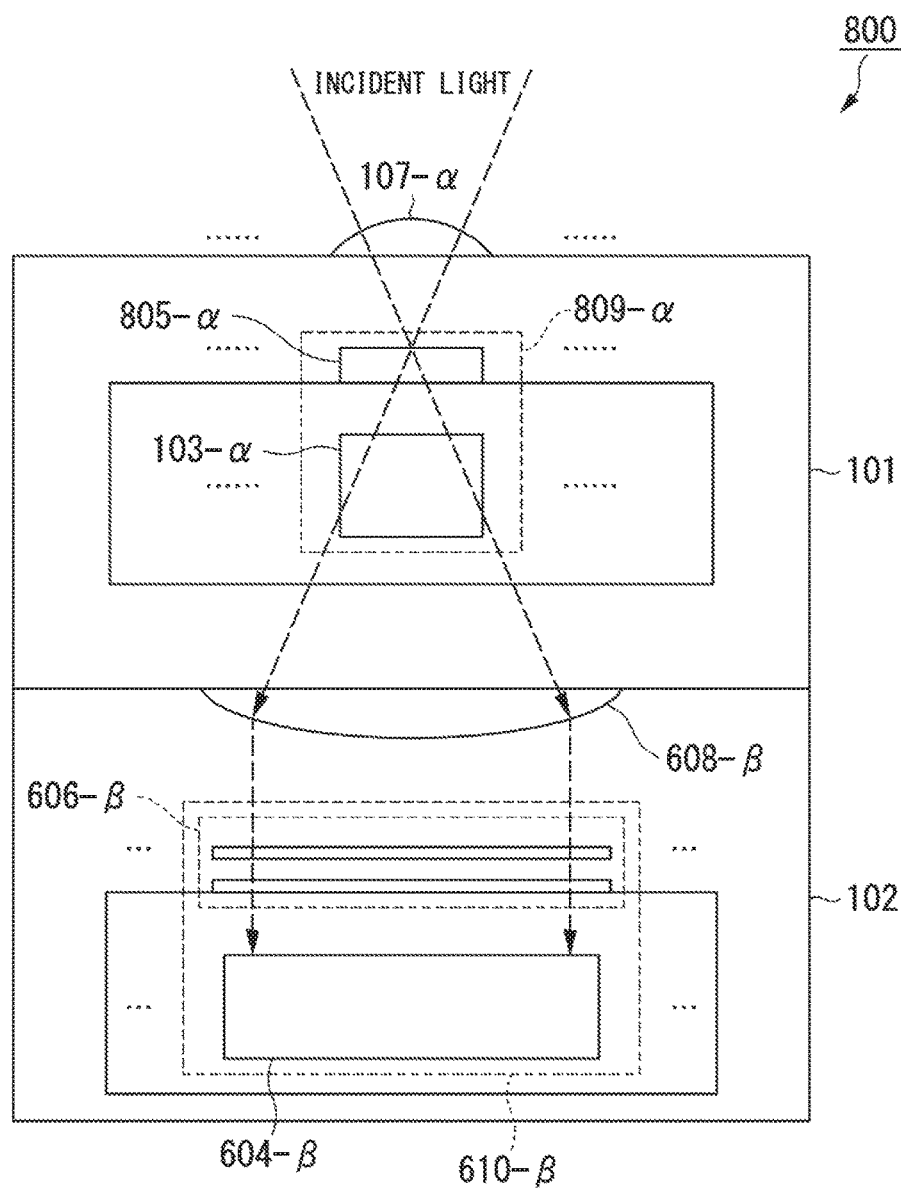
FIG. 18 is a sectional view showing a section of a place where a first pixel with a clear filter disposed therein is formed in the image-capturing element in the eighth embodiment of the invention.

FIG. 18 is a sectional view showing a section of a place where the first pixel 809 with the clear filter 805 disposed is formed in the image-capturing element 800 of this embodiment. In the example shown in FIG. 18, the image-capturing element 800 includes a first substrate 101, a second substrate 102, a first photodiode 103-α, a clear filter 805-α, a second photodiode 604-β, a Fabry-Perot filter 606-β, a first microlens 107-α, and a second microlens 608-β.

The first substrate 101, the second substrate 102, the first photodiode 103-α, the second photodiode 604-β, the Fabry-Perot filter 606-β, the first microlens 107-α, and the second microlens 608-β are the same as those in the sixth embodiment. The clear filter 805 transmits incident light directly without absorbing or reflecting light. The section of the place where the first pixel 109 with the color filter B disposed is formed is the same as in the sixth embodiment.

As described above, the second microlens 608 causes the entire light receiving surface of the second pixels 610 corresponding to the second microlens 608 to be irradiated vertically only with light transmitted through the first pixels 109, in which the color filter B transmitting blue light is disposed, or the first pixels 809, in which the clear filter 805 is disposed, among the first pixels 109. The color filter B which transmits blue light transmits more light. The clear filter 805 transmits incident light directly. Furthermore, it is possible to increase the area of the second pixels 610. Accordingly, the second pixels 610 can receive more light. Therefore, since the Fabry-Perot filters 606 are provided, even in the second pixels 610 having a narrow band of light and low sensitivity, it is possible to output sufficient second signals. Furthermore, it is possible to form the first pixels 809, in which the clear filter 805 is disposed, more easily than the through holes 709.

Since the first pixels 809 in which the clear filter 805 is disposed are provided, there is a region where the first pixel 109 is lacking; however, the signal processor 404 performs demosaic processing, thereby generating the first image based on the first signals.

Ninth Embodiment

Next, a ninth embodiment of the invention will be described. In this embodiment, an endoscope device embedded with one of the image-capturing devices described in the first embodiment to the eighth embodiment will be described.

Figure 19:
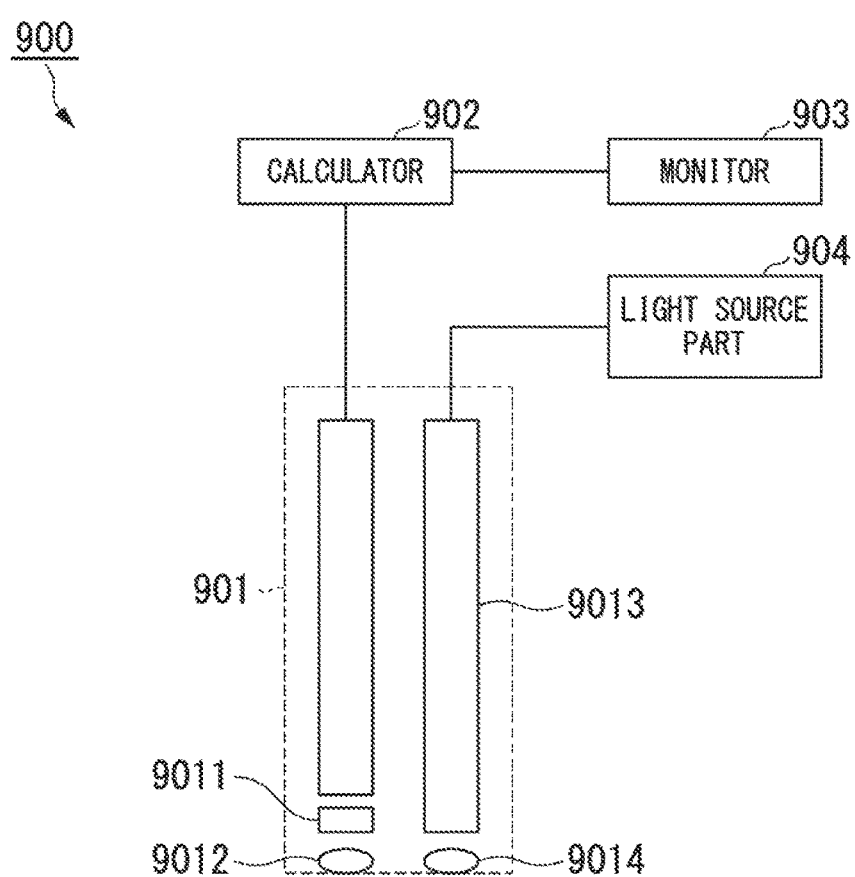
FIG. 19 is a block diagram showing the configuration of an endoscope device in a ninth embodiment of the invention.
Figure 20:
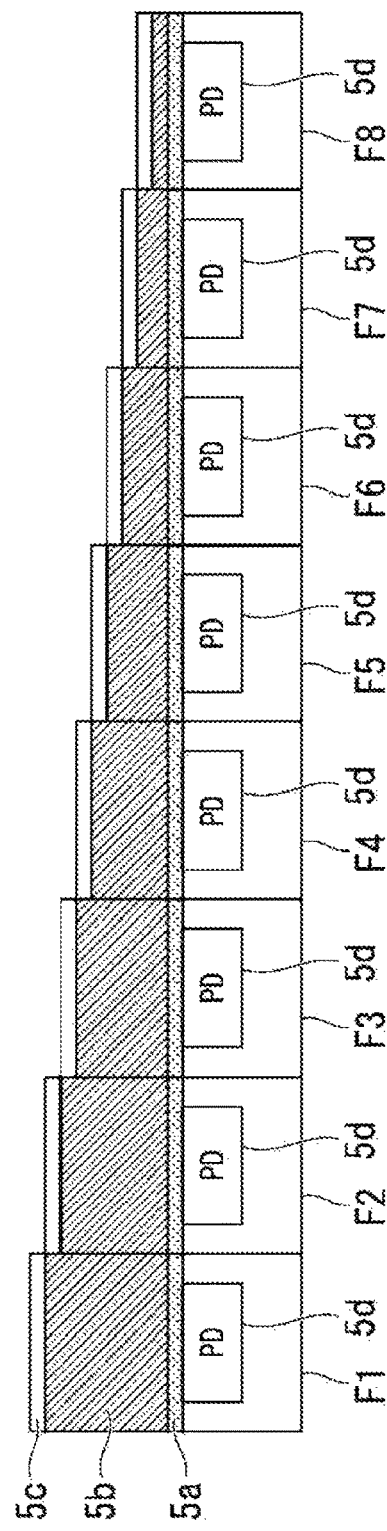
FIG. 20 is a schematic view showing an example of pixels, in each of which a Fabry-Perot filter is formed on a pixel of a conventional image sensor.
Figure 21:
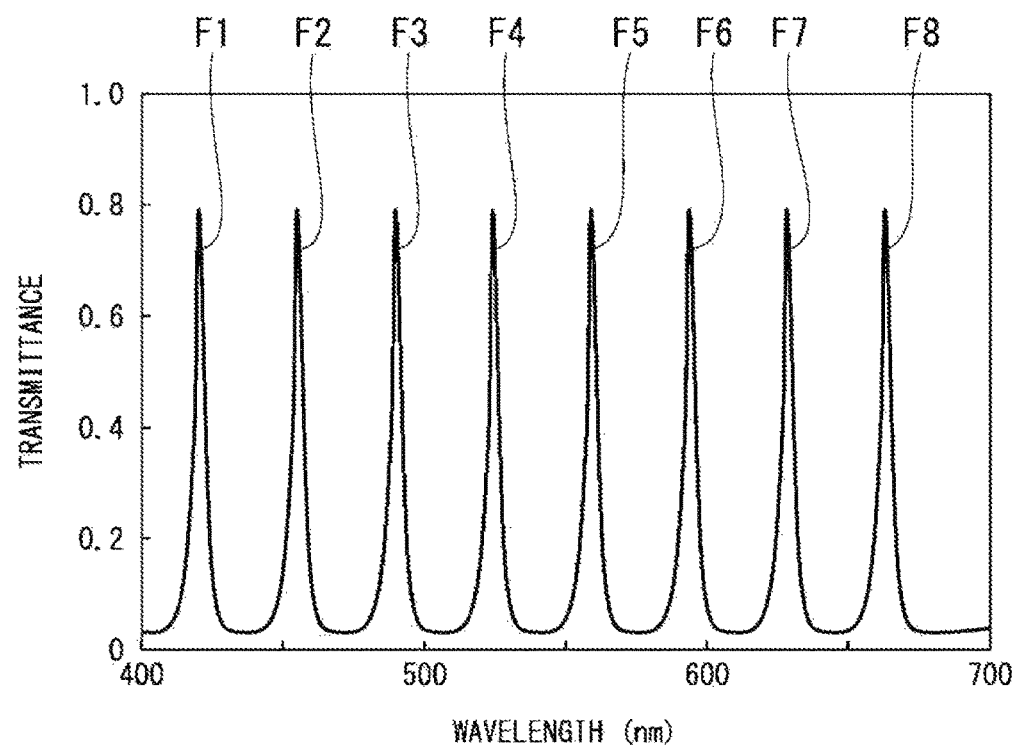
FIG. 21 is a graph showing the wavelength of light transmitted through a conventional Fabry-Perot filter.
Figure 22:
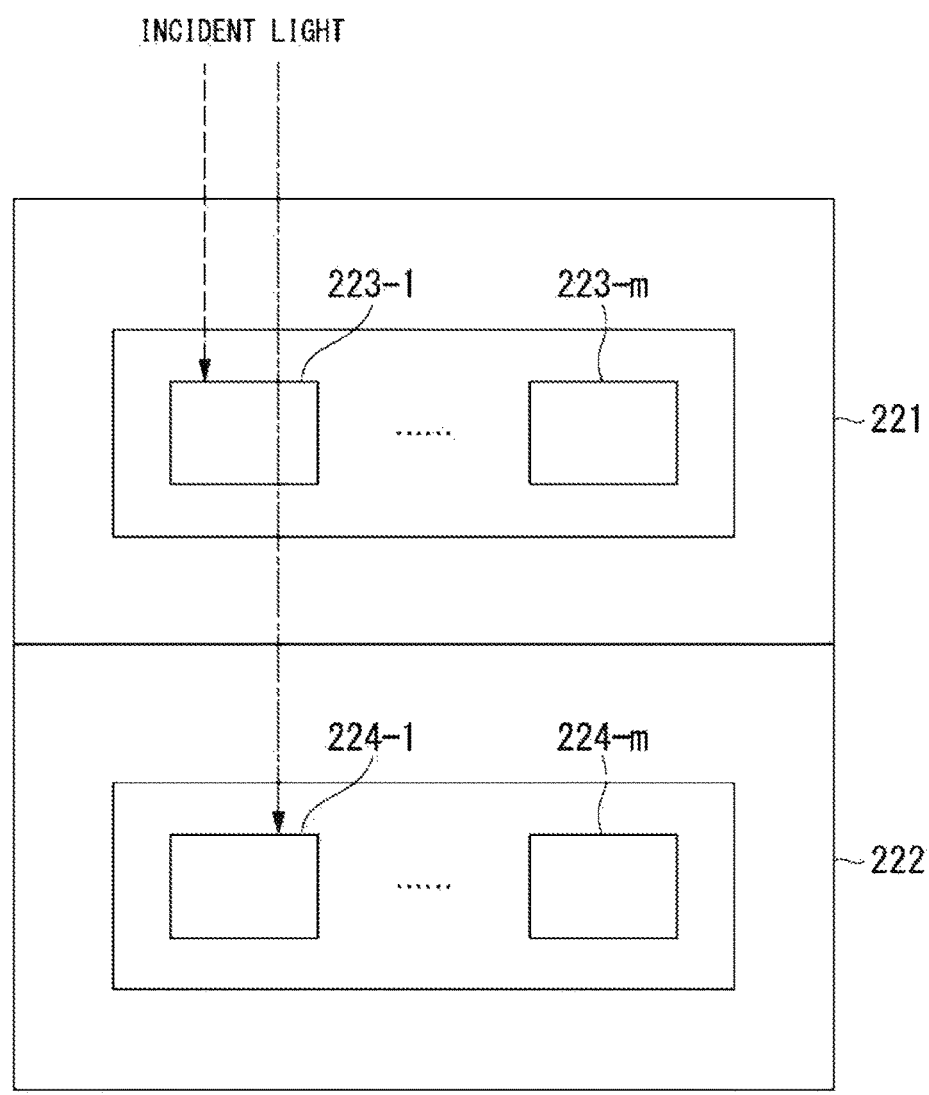
FIG. 22 is a sectional view showing a conventional image-capturing element with a hybrid structure in which two layers of an image-capturing element are laminated and imaging is also performed in a lower layer using light transmitted through an upper layer.
Figure 23:
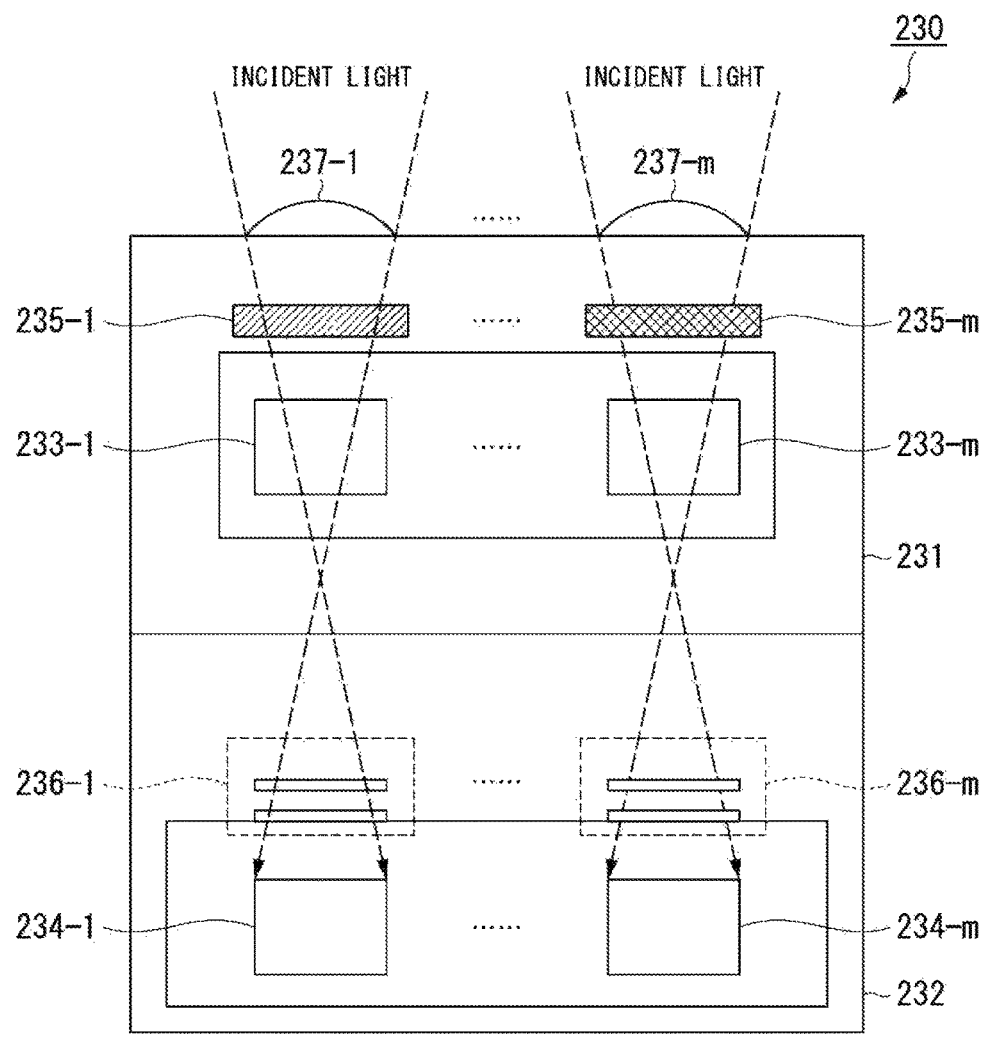
FIG. 23 is a sectional view showing an image-capturing element in which a Fabry-Perot filter is constituted on a lower substrate of a two-layered image-capturing element.
Figure 24:
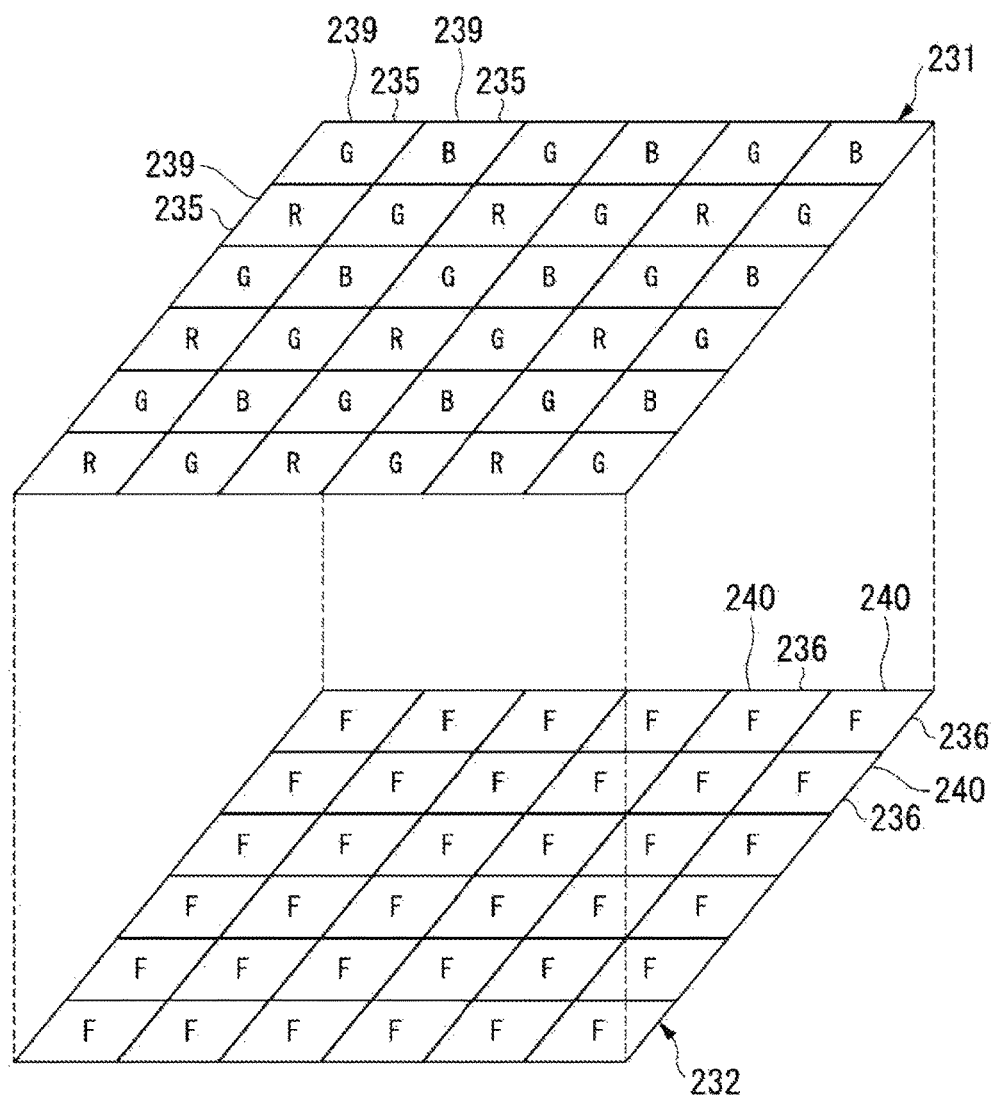
FIG. 24 is a schematic view showing the arrangement of color filters and the arrangement of Fabry-Perot filters.
Figure 25:
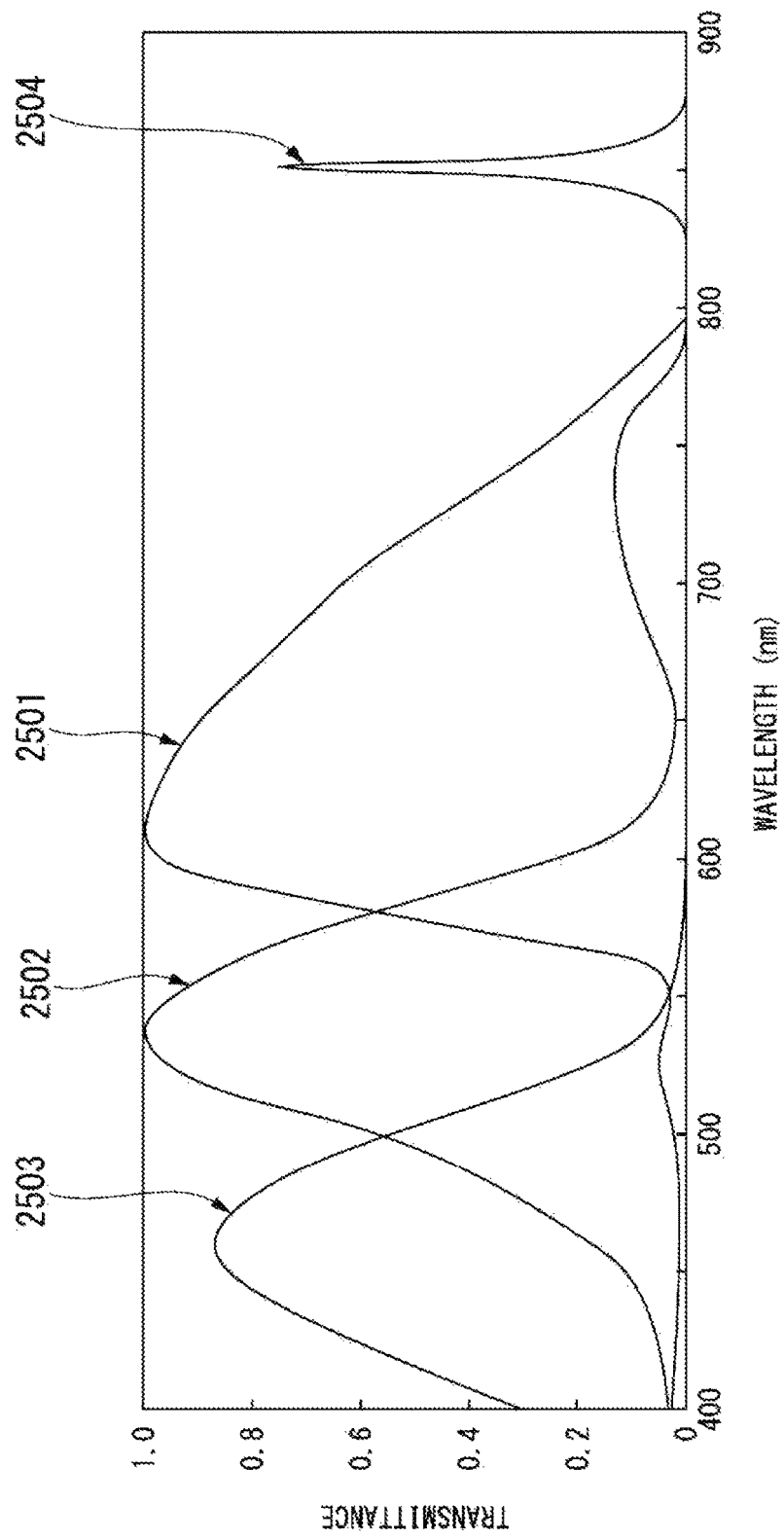
FIG. 25 is a graph showing the spectral characteristics of conventional color filters and a conventional Fabry-Perot filter.
Figure 26:
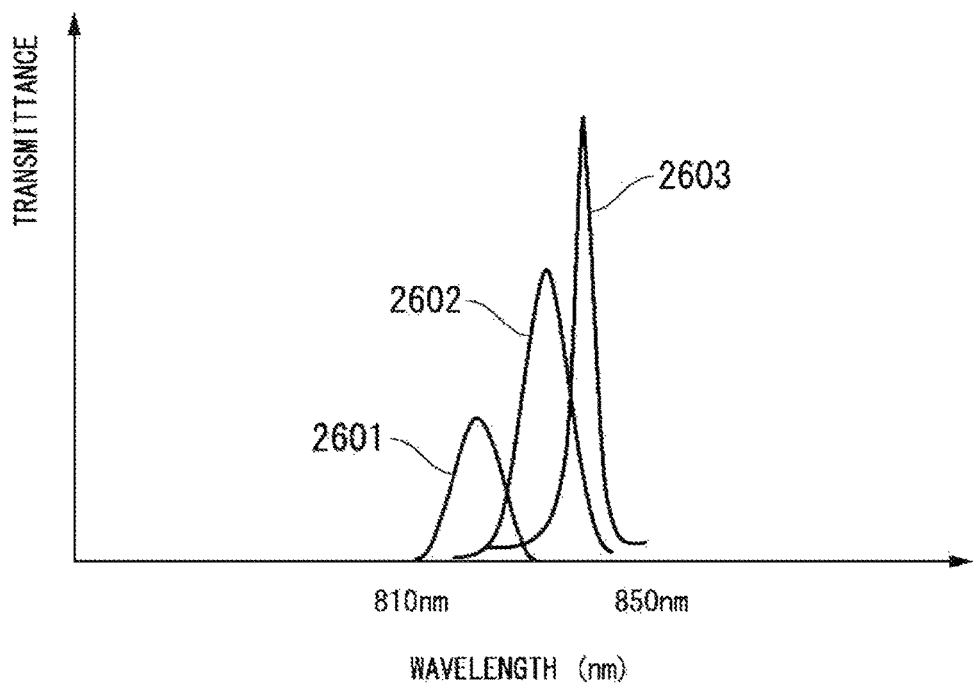
FIG. 26 is a graph showing angle dependence of a conventional Fabry-Perot filter.

FIG. 19 is a block diagram showing the configuration of the endoscope device in this embodiment. In the example shown in FIG. 19, an endoscope device 900 includes an endoscope 901, a calculator 902, a monitor 903, and a light source part 904. The calculator 902 controls the respective units of the endoscope device 900. The monitor 903 is, for example, a liquid crystal display, and displays an image. The light source part 904 is, for example, an LED, and emits light.

The endoscope 901 includes an image-capturing device 9011, an image-capturing lens 9012, a light guide 9013, and an illumination lens 9014. The image-capturing device 9011 is one of the image-capturing devices described in the first embodiment to the eighth embodiment. The image-capturing device 9011 is disposed in the tip portion of the endoscope 901. The image-capturing lens 9012 is disposed on the light receiving surface side of the image-capturing device 9011. The illumination lens 9014 is disposed in the tip portion of the endoscope 901.

The light guide 9013 irradiates the illumination lens 9014 with light emitted from the light source part 904. The illumination lens 9014 condenses light irradiated from the light guide 9013 and irradiates an object with condensed light. The image-capturing lens 9012 condenses light from the object and irradiates the image-capturing device 9011 with condensed light. The image-capturing device 9011 generates a first image and a second image based on light irradiated by the image-capturing lens 9012. The calculator 902 causes the monitor 903 to display the first image and the second image generated by the image-capturing device 9011.

For example, each of the image-capturing devices described in the first embodiment to the eighth embodiment can simultaneously capture a high-accuracy RGB image and a fluorescent image while achieving reduction in size. Accordingly, each of the image-capturing devices described in the first embodiment to the eighth embodiment is used in the endoscope device 900, whereby it is possible to simultaneously capture a high-accuracy RGB image and a fluorescent image. For example, it is possible to use a high-accuracy RGB image and a fluorescent image for cancer diagnosis or blood vessel observation at the time of a surgical operation.

Although the first embodiment to the ninth embodiment of the invention have been described in detail referring to the drawings, specific configurations are not limited to the embodiments, and may be modified in design without departing from the scope of the invention. For example, the configurations of the respective embodiments may be combined.

The image-capturing element of each embodiment has the first substrate, a plurality of first pixels, the second substrate, a plurality of second pixels, and a plurality of optical systems. A plurality of first pixels are disposed in a matrix on the first substrate, and each of the first pixels has the first light receiving element. The second substrate is disposed at a position overlapping the first substrate and on a side opposite to the light receiving surface side of the first substrate when viewed from the light receiving surface side of the first substrate. A plurality of second pixels are disposed on the second substrate, and each of the second pixels has the second light receiving element and the Fabry-Perot filter disposed on the light receiving surface side of the second light receiving element. A plurality of optical systems are disposed between the first substrate and a plurality of second pixels corresponding to a plurality of second pixels, and have negative refractive power. Therefore, in an image-capturing element with a hybrid structure, it is possible to capture a fluorescent image corresponding to a wavelength of interest with high accuracy.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. An image-capturing element comprising:
   a first substrate;
   a plurality of first pixels disposed in a matrix on the first substrate, each of the first pixels having a first light receiving element;
   a second substrate disposed at a position overlapping the first substrate and on a side opposite to a light receiving surface side of the first substrate when viewed from the light receiving surface side of the first substrate;
   a plurality of second pixels disposed in a matrix on the second substrate, each of the second pixels having a second light receiving element and a Fabry-Perot filter disposed on the light receiving surface side of the second light receiving element;
   a plurality of first optical systems disposed on the light receiving surface side of the first substrate, the first optical systems having a convex shape with the light receiving surface side as an upper surface, the first optical systems forming an incident light on the first light receiving element; and
   a plurality of second optical systems disposed corresponding to the plurality of second pixels between the first substrate and the plurality of second pixels, the second optical systems having a concave shape with the light receiving surface side as an upper surface, the second optical systems substantially collimating the incident light diffused after being imaged by the first light receiving element so as to be irradiated perpendicularly to a light receiving surface of the second pixel.

2. The image-capturing element according to claim 1, wherein a plurality of first microlenses respectively disposed on the light receiving surface side of the plurality of first pixels are provided.

3. The image-capturing element according to claim 1, wherein the plurality of optical systems are disposed on a surface opposite to the light receiving surface side of the first substrate.

4. The image-capturing element according to claim 1, wherein the plurality of optical systems are microlenses.

5. The image-capturing element according to claim 1, wherein each of the Fabry-Perot filters has any transmission band from a plurality of kinds of transmission bands.

6. The image-capturing element according to claim 1, wherein the plurality of optical systems are intralayer lenses.

7. The image-capturing element according to claim 1, wherein,
   among the plurality of optical systems,
   the closer the optical system is disposed to the center of the first substrate, the smaller the refractive power becomes, and
   the closer the optical system is disposed to the periphery of the first substrate, the larger the refractive power becomes.

8. The image-capturing element according to claim 1, wherein,
   among the plurality of optical systems,
   the closer the optical system is disposed to an optical axis of an imaging optical system, the smaller the refractive power becomes, and
   the further the optical system is disposed from the optical axis of the imaging optical system, the larger the refractive power becomes.

9. The image-capturing element according to claim 1, wherein
   each of the first pixels has a color filter disposed on the light receiving surface side of the first light receiving element,
   the color filters are disposed in a Bayer array, and
   the plurality of second pixels and the plurality of optical systems are disposed so as to overlap the color filters transmitting blue light when viewed from the light receiving surface side of the first substrate.

10. The image-capturing element according to claim 1, wherein
    each of the first pixels has a color filter disposed on the light receiving surface side of the first light receiving element,
    the color filters are disposed in a Bayer array,
    a part of the first pixels in which color filters transmitting green light are disposed is provided as through holes, and
    the plurality of second pixels and the plurality of optical systems are disposed so as to overlap the through holes when viewed from the light receiving surface side of the first substrate.

11. The image-capturing element according to claim 1, wherein
    each of the first pixels has a color filter disposed on the light receiving surface side of the first light receiving element,
    the color filters are disposed in a Bayer array,
    a part of the color filters transmitting green light is removed, and
    the plurality of second pixels and the plurality of optical systems are disposed so as to overlap the first pixels with the color filters removed when viewed from the light receiving surface side of the first substrate.

12. The image-capturing element according to claim 1, wherein the first substrate, the plurality of first pixels, the second substrate, the plurality of second pixels, and the plurality of optical systems are disposed at the tip of an endoscope.

13. The image-capturing element according to claim 1, wherein the plurality of second pixels are disposed at positions facing the plurality of first pixels, respectively.

14. The image-capturing element according to claim 1, wherein the plurality of optical systems refracts light transmitted through the first pixel so as to be irradiated perpendicularly to a light receiving surface of the second pixel.

* * * * *